United States Patent
Lee et al.

(10) Patent No.: US 10,390,806 B2
(45) Date of Patent: Aug. 27, 2019

(54) DEVICES, SYSTEMS, AND METHODS FOR OBTAINING A TISSUE SAMPLE USING A BIOPSY TOOL

(71) Applicant: COVIDIEN LP, Mansfield, MA (US)

(72) Inventors: Michael Lee, Santa Rosa, CA (US);
William Krimsky, Bel Air, MD (US)

(73) Assignee: COVIDIEN LP, Mansfield, MA (US)

( * ) Notice: Subject to any disclaimer, the term of this patent is extended or adjusted under 35 U.S.C. 154(b) by 657 days.

(21) Appl. No.: 14/664,318

(22) Filed: Mar. 20, 2015

(65) Prior Publication Data

US 2015/0272556 A1    Oct. 1, 2015

Related U.S. Application Data

(60) Provisional application No. 61/971,812, filed on Mar. 28, 2014.

(51) Int. Cl.
| | | |
|---|---|---|
| *A61B 10/04* | (2006.01) | |
| *A61M 25/01* | (2006.01) | |
| *A61B 1/018* | (2006.01) | |
| *A61B 10/00* | (2006.01) | |

(Continued)

(52) U.S. Cl.
CPC .............. *A61B 10/04* (2013.01); *A61B 1/018* (2013.01); *A61B 10/0096* (2013.01); *A61B 10/0266* (2013.01); *A61B 10/0283* (2013.01); *A61B 10/06* (2013.01); *A61M 25/0136* (2013.01); *A61M 25/0138* (2013.01);

(Continued)

(58) Field of Classification Search
None
See application file for complete search history.

(56) References Cited

U.S. PATENT DOCUMENTS 4,640,296 A * 2/1987 Schnepp-Pesch ............ A61B 10/0283
600/567
4,781,202 A 11/1988 Janese
(Continued)

FOREIGN PATENT DOCUMENTS

CN    102481146 A    5/2012
CN    102793576 A    11/2012
(Continued)

OTHER PUBLICATIONS

"Spiral", www.merriam-webster.com/dictionary/spiral, printed Apr. 19, 2018, 7 pages.*
(Continued)

*Primary Examiner* — Matthew Kremer

(57) ABSTRACT

A biopsy assembly including a biopsy catheter having a proximal portion and a distal portion, a navigation catheter configured to receive the biopsy catheter for positioning the biopsy catheter adjacent target tissue, wherein the biopsy catheter is configured to be received within the navigation catheter, a coring component, and an anchoring component configured to anchor the biopsy catheter to target tissue. The coring component includes a proximal region and a distal region, the distal region formed of one or more distally extending blades and the proximal region being coupled to the distal portion of the biopsy catheter and the one or more blades are configured to penetrate target tissue and sever a tissue sample from the target tissue.

20 Claims, 22 Drawing Sheets

(51) Int. Cl.
*A61B 10/02* (2006.01)
*A61B 10/06* (2006.01)

(52) U.S. Cl.
CPC . *A61M 25/0147* (2013.01); *A61B 2010/0208* (2013.01); *A61B 2010/045* (2013.01)

(56) References Cited

U.S. PATENT DOCUMENTS

| | | | |
|---|---|---|---|
| 4,785,826 A * | 11/1988 | Ward | A61B 10/025 30/174 |
| 4,926,877 A | 5/1990 | Bookwalter | |
| 5,074,311 A | 12/1991 | Hasson | |
| 5,133,360 A | 7/1992 | Spears | |
| 5,152,744 A * | 10/1992 | Krause | A61B 17/32002 604/22 |
| 5,183,052 A | 2/1993 | Terwilliger | |
| 5,267,572 A | 12/1993 | Bucalo | |
| 5,649,908 A | 7/1997 | Itoh | |
| 5,823,971 A | 10/1998 | Robinson et al. | |
| 5,848,978 A | 12/1998 | Cecchi | |
| 6,007,495 A | 12/1999 | Matula | |
| 6,007,544 A | 12/1999 | Kim | |
| 6,068,603 A | 5/2000 | Suzuki | |
| 6,083,237 A | 7/2000 | Huitema et al. | |
| 6,110,127 A | 8/2000 | Suzuki | |
| 6,139,508 A | 10/2000 | Simpson et al. | |
| 6,213,957 B1 | 4/2001 | Milliman et al. | |
| 6,315,737 B1 | 11/2001 | Skinner | |
| 6,755,793 B2 | 6/2004 | Lamoureux et al. | |
| 6,792,305 B2 | 9/2004 | Rastorgoueff et al. | |
| 6,875,183 B2 | 4/2005 | Cervi | |
| 7,001,342 B2 | 2/2006 | Faciszewski | |
| 7,033,324 B2 | 4/2006 | Giusti et al. | |
| 7,137,956 B2 | 11/2006 | Nishtalas et al. | |
| 7,229,439 B2 | 6/2007 | Burbank et al. | |
| 7,278,970 B2 | 10/2007 | Goldenberg | |
| 7,311,673 B2 | 12/2007 | Mueller, Jr. et al. | |
| 8,449,478 B2 | 5/2013 | Lee et al. | |
| 2003/0225364 A1* | 12/2003 | Kraft | A61B 10/025 604/35 |
| 2007/0088230 A1* | 4/2007 | Terashi | A61B 17/3207 600/585 |
| 2009/0287114 A1* | 11/2009 | Lee | A61B 10/0266 600/566 |
| 2011/0208089 A1* | 8/2011 | Sundheimer | A61B 10/0233 600/567 |
| 2012/0172915 A1* | 7/2012 | Fifer | A61F 2/013 606/200 |
| 2013/0225997 A1 | 8/2013 | Dillard et al. | |

FOREIGN PATENT DOCUMENTS

| | | |
|---|---|---|
| EP | 0 667 126 A1 | 8/1995 |
| EP | 1520518 A2 | 4/2005 |
| WO | 9508291 A1 | 3/1995 |
| WO | 2008115526 A2 | 9/2008 |

OTHER PUBLICATIONS

European Search Report issued in Application No. 15 16 1339 dated Jun. 15, 2015.
European Examination Report issued in Appl. No. 15161339.5 dated Jun. 7, 2018 (6 pages).
Australian Examination Report No. 1 issued in corresponding Appl. No. AU 2015201540 dated Dec. 18, 2018 (3 pages).
Chinese Office Action issued in corresponding Appl. No. CN 201510142875.X dated Feb. 2, 2019, together with English language translation (19 pages).

* cited by examiner

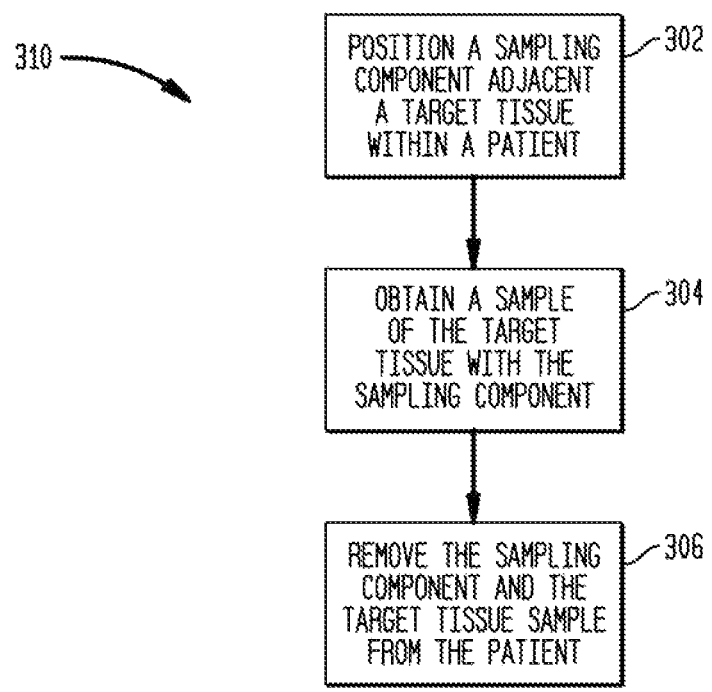

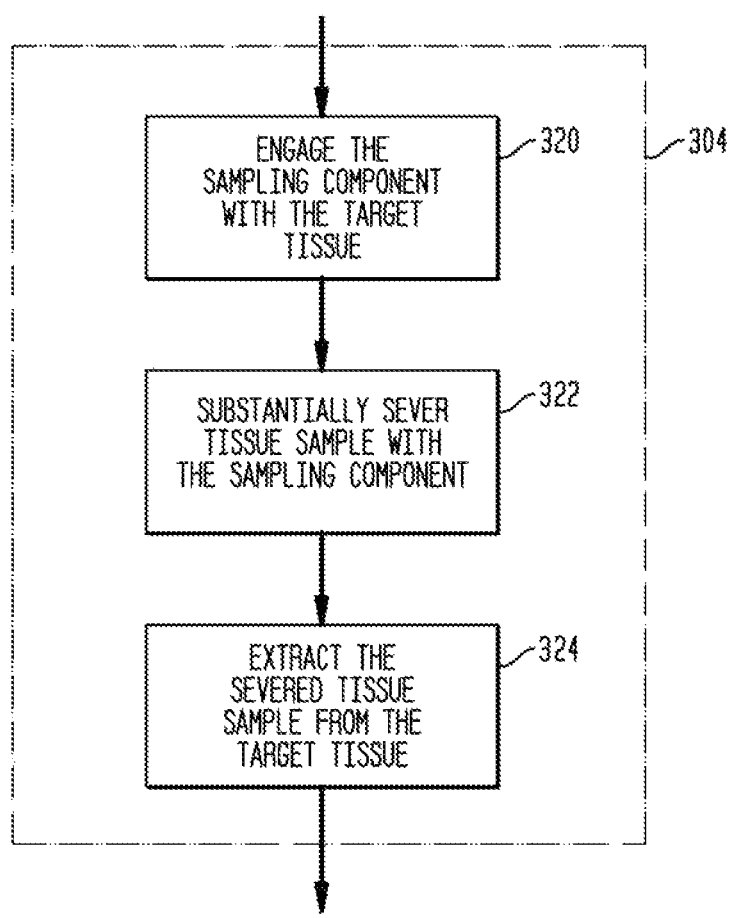

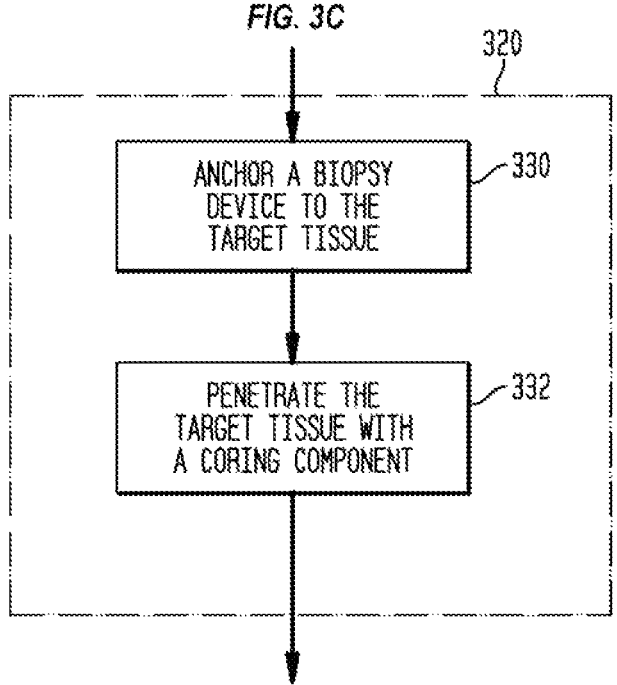

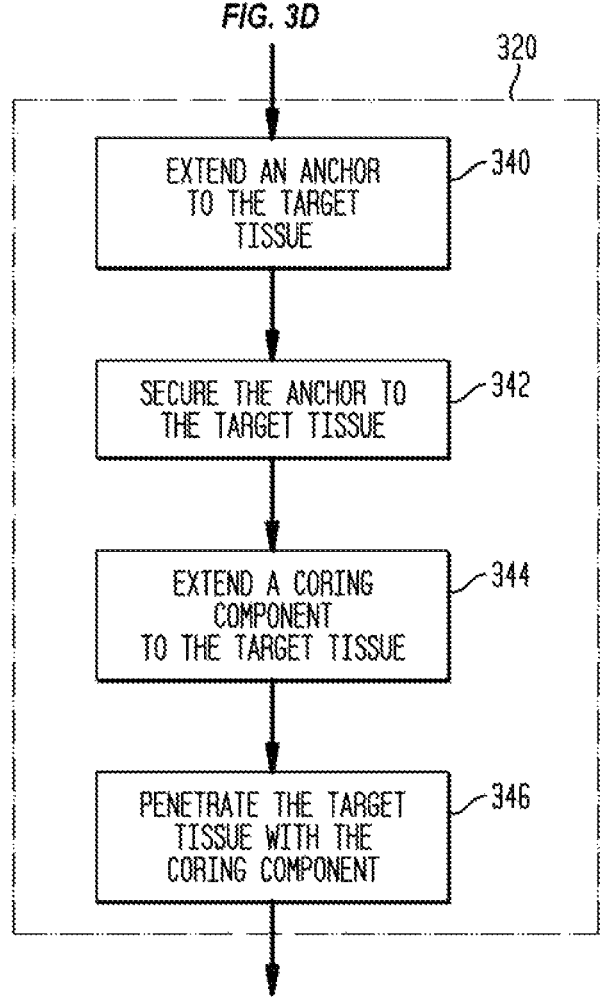

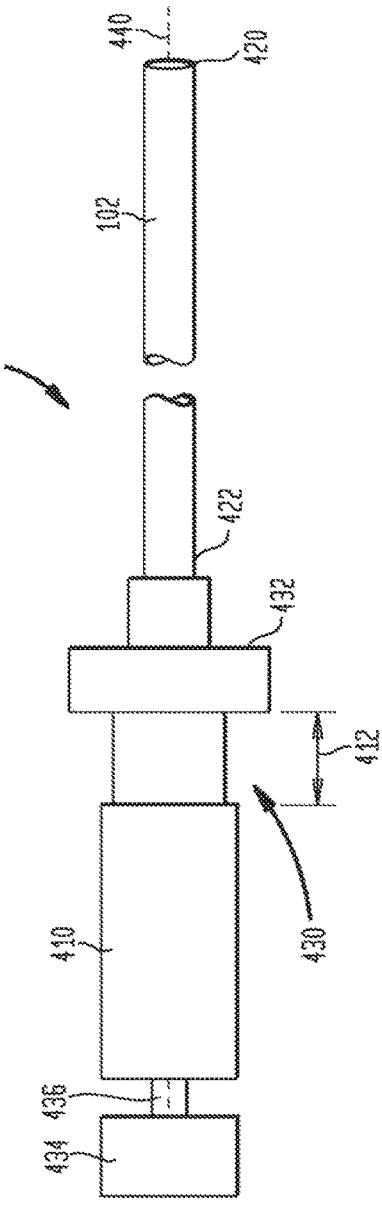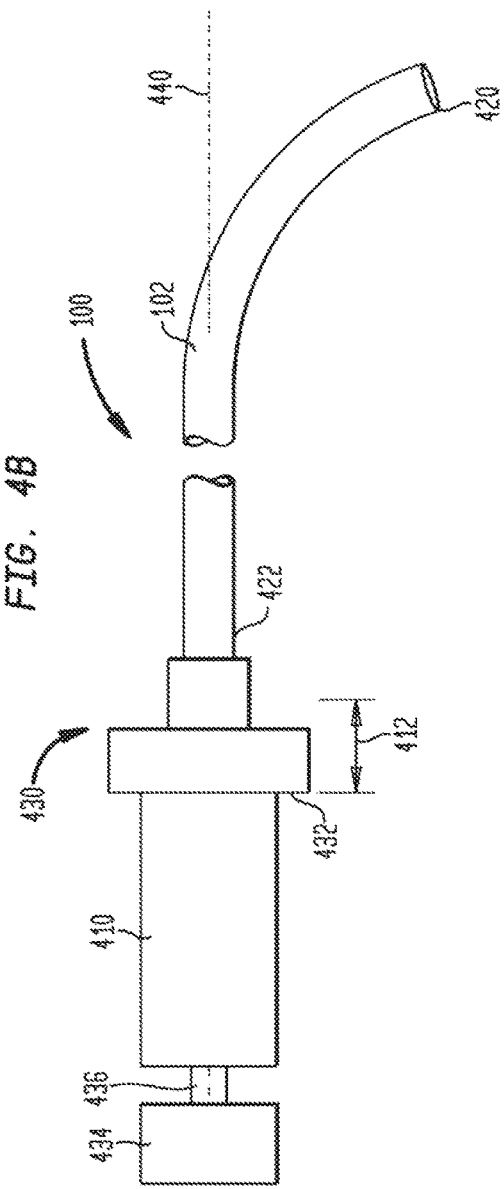

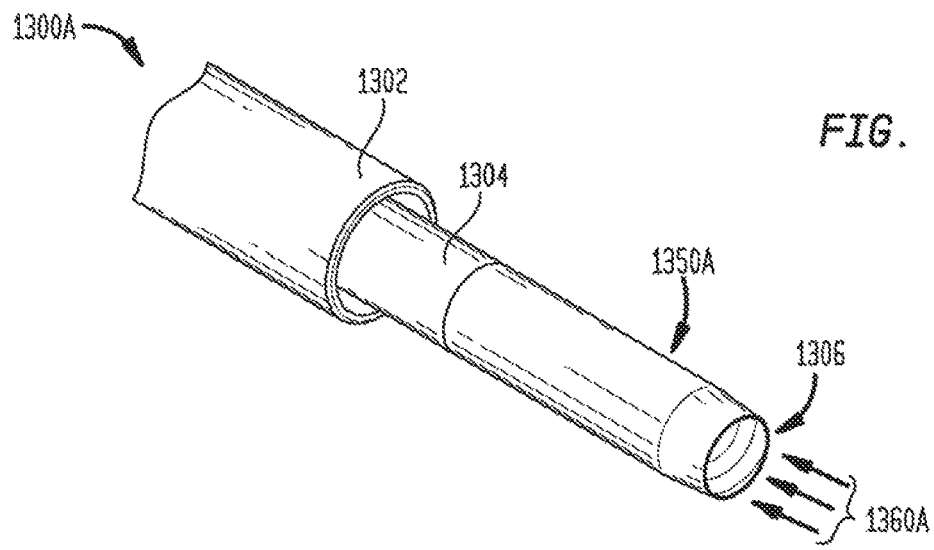
FIG. 13A
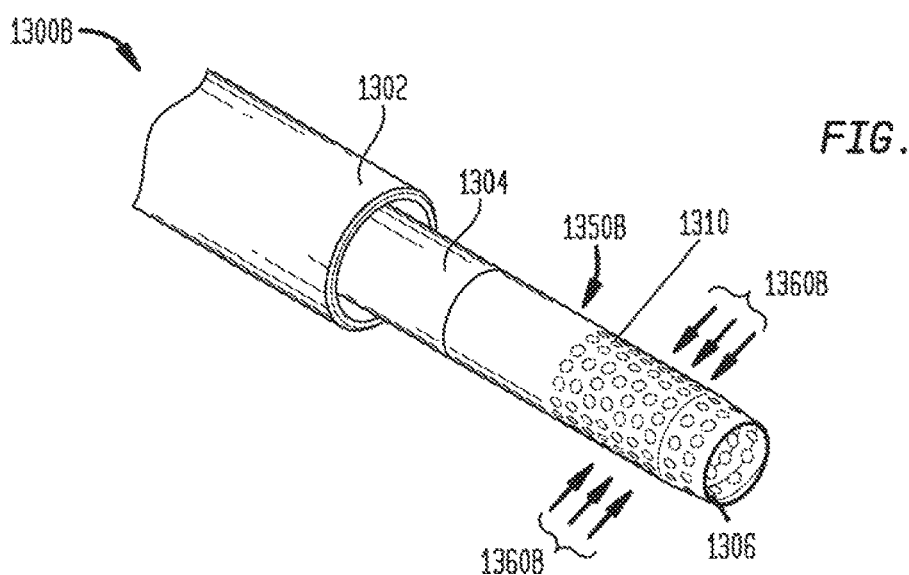
FIG. 13B
FIG. 13C
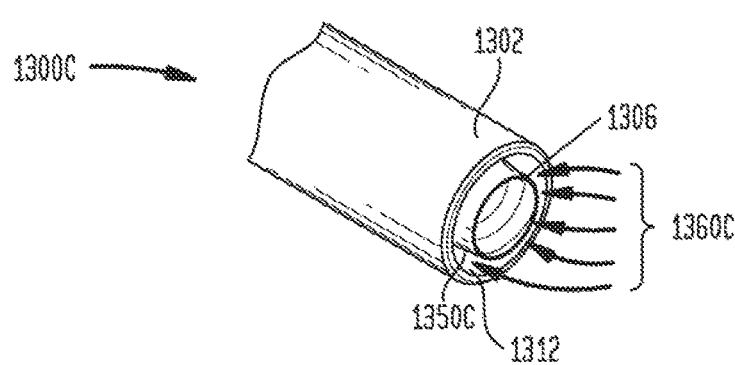

DEVICES, SYSTEMS, AND METHODS FOR OBTAINING A TISSUE SAMPLE USING A BIOPSY TOOL

CROSS REFERENCE TO RELATED APPLICATION

The present application claims the benefit of and priority to U.S. Provisional Application Ser. No. 61/971,812, filed on Mar. 28, 2014, the entire contents of which are incorporated herein by reference.

BACKGROUND

Technical Field

The present disclosure relates generally to a tissue-sampling device, and more particularly, to a biopsy device insertable through a working channel of an endoscope or bronchoscope.

Description of Related Art

For various medical reasons, e.g. diagnostic tests, it is often necessary for a physician, surgeon or other medical practitioner to obtain a sample of a patient's body. During these sampling or biopsy procedures, the samples may be taken from a variety of organs and other soft tissue, or from a more rigid structure such as a bone or bone marrow.

There are a variety of medical procedures to obtain a tissue sample. For example, an endoscopic procedure commonly referred to as an endoscopic biopsy procedure, is often used to obtain tissue samples within a patient's body. During an endoscopic biopsy procedure, a sample of a target tissue is removed from a patient with an endoscopic biopsy device having a tissue acquisition element. The endoscopic biopsy device may include an endoscope having a lighted camera on a distal end that is used by the surgeon to view the target tissue during the biopsy procedure. Other devices or systems for visualizing the sampling procedure may also be used. For example, any radiographic, fluoroscopic, or other navigational or guidance modality, may also be used for visualizing the sampling procedure.

In certain devices, the biopsy or tissue acquisition element may be passed through a catheter that is separate from the endoscope having a camera thereon. Likewise, other devices may also be inserted through or around the endoscope.

In another example, a bronchoscope is used to assist in obtaining tissue samples within a patient's body. In such a procedure, a bronchoscope is inserted into a patient's airways through the patient's nose or mouth. A typical bronchoscope includes an illumination assembly for illuminating the region distal to the bronchoscope's tip, an imaging assembly for providing a video image from the bronchoscope's tip, and a working channel through which instruments, e.g., diagnostic instruments such as biopsy tools and/or therapeutic instruments such as ablation probes, can be inserted.

Bronchoscopes are limited in how far they may be advanced through the airways due to their size. Where the bronchoscope is too large to reach a target location deep in the lungs, a catheter or extended working channel can be extended out of the working channel to navigate to the target. A sensor, either attached to the catheter, or formed on a locatable guide ("LG") passed through the catheter may be utilized to navigate from the end of the bronchoscope to the target location. That is, the sensor together with a navigation system, enables the position and orientation of the sensor to be tracked as it is advanced through the airways. One such system is described in U.S. Provisional Application No. 62/020,240, titled "System and Method for Navigating Within the Lung", filed Jul. 2, 2014, the entire contents of which are hereby incorporated by reference.

When an LG is used, the LG/catheter combination is inserted through the working channel of the bronchoscope and into the patient's airways. Once the combination LG has been navigated to the target location, aided by the position and orientation tracking provided by the navigation system, the LG may be retracted through the catheter, leaving the catheter in position. As noted above, the catheter is often referred to as an extended working channel ("EWC") because it effectively functions as an extension of the working channel of the bronchoscope.

Once the LG has been retracted from the EWC, the EWC may be used as an avenue for guiding working tools, e.g., biopsy tools, ablation probes, etc., to the target location. During a biopsy, a sample of the target tissue may be taken using a biopsy brush or a needle when performing Fine Needle Aspiration procedures. Following sampling of the target tissue, the tissue sample is removed from the patient and examined. The tissue is generally examined under a microscope by a pathologist or chemically analyzed using, for example, gas chromatography techniques.

Depending on the target tissue and other physical conditions or circumstances, sampling of internal tissue may be difficult or may require skill to quickly and efficiently obtain an adequate tissue sample to permit proper examination by a pathologist or other medical practitioner.

SUMMARY

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

Provided in accordance with the present disclosure is a biopsy assembly including a biopsy catheter having a proximal portion and a distal portion, a navigation catheter configured to receive the biopsy catheter for positioning the biopsy catheter adjacent target tissue, wherein the biopsy catheter is configured to be received within the navigation catheter. The biopsy assembly also includes a coring component and an anchoring component configured to anchor the biopsy catheter to target tissue. The coring component includes a proximal region and a distal region, the distal region formed of one or more distally extending blades and the proximal region being coupled to the distal portion of the biopsy catheter, wherein the one or more blades are configured to penetrate target tissue and sever a tissue sample from the target tissue.

According to aspects of the disclosure the navigation catheter is configured to be received within a working channel of an endoscope. Further the biopsy catheter and the coring component have a continuous lumen therein and a suction device coupled to the proximal end of the biopsy catheter and configured to provide suction to the distal end of the coring component. The biopsy assembly may further include a suction tube having a distal end and a proximal end, the proximal end is coupled to the suction device and the distal end configured to secure the tissue sample, wherein the distal end of the suction tube includes a suction bay configured to hold the severed tissue sample.

According to further aspects of the disclosure, the navigation catheter is flexible and contains one or more pull wires having a distal end and a proximal end configured to cause the distal end of the navigation catheter to deflect in at least one direction. The proximal end of the biopsy catheter may be coupled to a handle, wherein the rotation of the handle causes the biopsy catheter to rotate.

According to further aspects of the disclosure, the proximal portion of the coring component contains at least one slit configured to provide the coring component the flexibility to deflect in at least one direction. The slits may be alternating slits perpendicular to a longitudinal axis of the coring component. Alternatively, the slits may be diagonal slits. Further the coring component may contain at least one row of parallel slits with equal length.

According to a further aspect of the disclosure, the distal end of the pull wire is coupled to the distal end of the navigation catheter and the proximal end is coupled to a control mechanism and configured to cause the distal end of the navigation catheter to deflect in one or more directions.

In yet further aspects of the disclosure the anchoring component includes a first needle and a second needle, wherein the coring component is configured to advance through the navigation catheter between first needle and the second needle.

In at least one embodiment of the disclosure he coring component includes a first blade and a second blade, wherein the first blade is configured to anchor the coring component onto the target tissue and the second blade is configured to slice at least a part of the target tissue. Alternatively, the coring component may include two or more elongate blades, wherein each blade is disposed in a spiral configuration.

In accordance with the present disclosure the anchoring component may be a needle having proximal end and a distal end, wherein the distal end is curved.

BRIEF DESCRIPTION OF THE DRAWINGS

Various aspects and features of the present disclosure are described hereinbelow with references to the drawings, wherein:

FIG. 3A is a high-level flowchart illustrating an exemplary sampling procedure in accordance with embodiments of the present disclosure;

FIG. 3B is a mid-level flowchart illustrating the obtaining a sample of a target tissue in accordance with embodiments of block 204 of FIG. 3A;

FIG. 3C is a detailed flowchart illustrating the engagement of a sampling component with a target tissue in accordance with one embodiment of block 220 of FIG. 3B;

FIG. 3D is a detailed flowchart illustrating the engagement of a sampling component with a target tissue in accordance with one embodiment of block 220 of FIG. 3B;

FIG. 4A is a simplified side view of one embodiment of a biopsy device which may be used by a surgeon to position a sampling component at a desired location within a patient;

FIG. 4B is a simplified side view of the embodiment of components of a biopsy device shown in FIG. 4A in which the distal region of the device is shown in a curved configuration;

FIG. 13A is a perspective view of a biopsy device having an anchoring element in accordance with one embodiment of the present disclosure;

FIG. 13B is a perspective view of a biopsy device having an anchoring element in accordance with one embodiment of the present disclosure; and FIG. 13C is a perspective view of a biopsy device having an anchoring element in accordance with one embodiment of the present disclosure.

DETAILED DESCRIPTION

Devices, systems, and methods for navigating a biopsy tool to a target location and obtaining a tissue sample using the biopsy tool are provided in accordance with the present disclosure and described in detailed below.

Aspects of the present disclosure are generally directed to a biopsy device having a coring component configured to engage target tissue of a patient and to remove a sample of the target tissue from the patient. The coring component comprises a longitudinal lumen terminating in a distal opening. A distal region of the coring component is formed of one or more distally extending blades each having a distal end positioned around the distal opening of the lumen. The blades are configured to penetrate the target tissue such that a tissue sample having a cross-section defined by the distal ends of the one or more blades is received within the lumen of the coring component via the distal opening. The blades are configured to substantially sever the tissue sample from the remainder of the target tissue.

In certain embodiments, the coring component comprises two or more elongate blades each having distal ends positioned around the distal opening. In some embodiments, to sever the tissue, one or more of the blades flex inwardly towards a longitudinal axis of the coring component. In the same or other embodiments, the coring component is rotatable relative to the target tissue to facilitate the severing of the tissue sample. In particular embodiments of the present disclosure, the biopsy device comprises an anchoring element which secures the device to the target tissue. In certain embodiments, the biopsy device may further include a tissue retention feature which secures the tissue sample in the lumen of the coring component.

Figure 1:
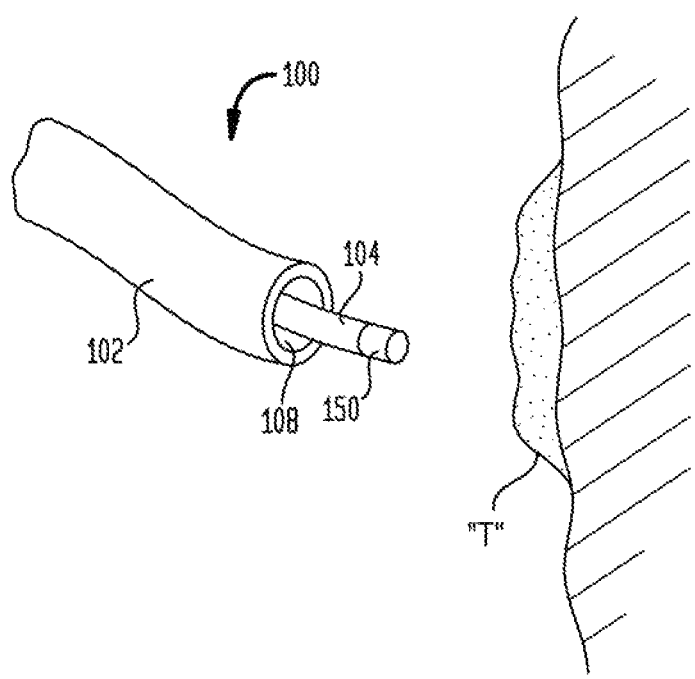
FIG. 1 is a perspective view of a distal end of an exemplary biopsy device in accordance with embodiments of the present disclosure.

FIG. 1 is a perspective view of a distal region of an exemplary navigation tool 100 that may be used to sample a target tissue "T" within a patient in accordance with embodiments of the present disclosure. Although the present disclosure will be discussed herein with reference to specific types of biopsy devices and procedures, namely endoscopic biopsy devices and procedures, it should be appreciated that embodiments of the present disclosure may be used in conjunction with any other biopsy or tissue sampling device/procedure.

In certain embodiments of the present disclosure, a navigation tool 100 comprises a navigation catheter 102 which is introduced into the patient to facilitate the positioning of sampling component 150 adjacent target tissue "T". The target tissue "T" comprises a tissue which the surgeon desires to obtain a sample thereof. In accordance with embodiments of the present disclosure, the target tissue "T" may be a portion of a tissue, bone or organ surface, a portion of the tissue, bone or organ lying beneath the surface, or any other portion of a tissue, organ or bone.

In embodiments in which navigation catheter 102 is provided, biopsy catheter 104 may be introduced into a lumen 108 of navigation catheter 102. As would be appreciated, biopsy catheter 104 may be introduced into lumen 108 during a biopsy procedure or biopsy catheter 104 may be preoperatively positioned within lumen 108. Regardless whether biopsy catheter 104 is introduced into lumen 108 prior to or during a biopsy procedure, it should be appreciated that biopsy catheter 104 is movable within navigation catheter 102 and may be extended from a distal end of the navigation catheter 102.

FIG. 1 illustrates an embodiment of navigation tool 100 in which biopsy catheter 104 extends from the distal end of navigation catheter 102. In the illustrated embodiment, a sampling component 150 is integrated at the distal end of biopsy catheter 104. Sampling component 150 is configured to obtain a sample of a patient's target tissue 130. Sampling component 150 may be a brush, blade, needle, or any other component capable of taking a tissue sample.

Figure 2A:
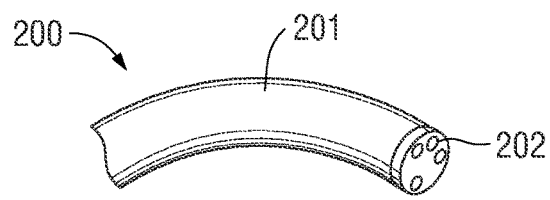
FIG. 2A is a perspective view of a distal end of an exemplary endoscope including an endoscope having a lighted camera on a distal end.
Figure 2B:
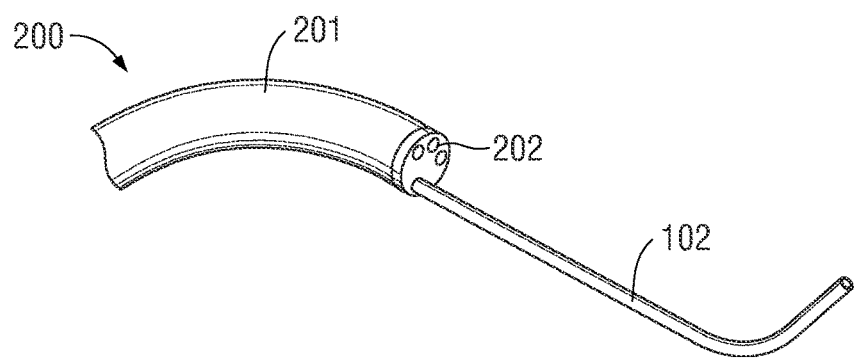
FIG. 2B is a perspective view of a navigation catheter that is passed through the endoscope shown in FIG. 2.
Figure 2C:
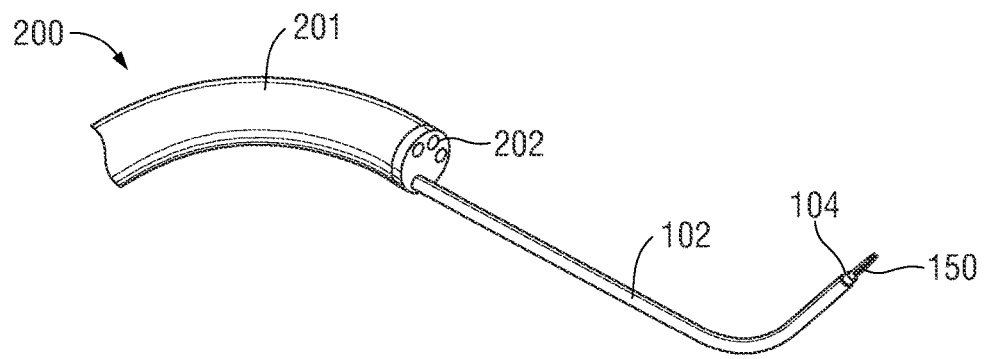
FIG. 2C is a perspective view of a biopsy device that is passed through and extends past the distal end of the navigation catheter shown in FIG. 2B.

FIG. 2A is a perspective view of a distal region of an exemplary endoscopic biopsy device 200 including an endoscope 201 having a lighted camera 202 on a distal end. Navigation catheter 102 is positioned within, and extends past the distal end of, endoscope 201, as shown in FIG. 2B. As shown in FIG. 2C, a biopsy catheter 104, with a sampling component 150 located at the distal end of biopsy catheter 104, is further positioned within navigation catheter 102 and extends past the distal end of navigation catheter 102. Navigation catheter 102 is inserted into endoscope 201 to navigate further towards target tissue "T." Once positioned adjacent target tissue "T," navigation catheter 102 may be used as an avenue for guiding working tools, including biopsy catheter 104. In some embodiments, a locatable guide (LG) is inserted into navigation catheter 102 to navigate the catheter to the target tissue "T." Once the navigation catheter 102 has been navigated to the target tissue "T," LG is retracted, leaving the navigation catheter 102 in position. Alternatively, the navigation catheter 102 or the biopsy catheter 104 may have a sensor embedded therein to enable tracking and navigation to the target "T". In embodiments, endoscope 201 may include a fiber optic scope.

FIG. 3A is a high-level flowchart illustrating a surgical procedure 310 for obtaining a tissue sample from a patient, in accordance with embodiments of the present disclosure. At block 302, a sampling component is positioned adjacent a target tissue within the patient. Embodiments of a biopsy device having components to position a sampling component adjacent the target tissue are described below with reference to FIGS. 4A and 4B.

At block 304, the sampling component is used to obtain a tissue sample from the target tissue. Obtaining a tissue sample is described in more detail below with reference to FIG. 3B. At block 306, after a tissue sample is obtained, the sampling component and the tissue sample are removed from the patient.

FIG. 3B is a mid-level flowchart illustrating the operations performed to obtain a tissue sample in accordance with embodiments of block 304 of FIG. 3A. At block 320, the sampling component engages the target tissue. FIGS. 3C and 3D illustrate various embodiments for engaging the target tissue with the sampling component.

At block 322, the sampling component substantially severs a portion of the tissue sample from the remainder if the target tissue. Substantial severing of the tissue sample from the target tissue is described below with reference to FIGS. 5-8C At block 324, the severed tissue sample is extracted from the target tissue.

FIG. 3C is a flowchart illustrating particular embodiments of block 320 of FIG. 3B in which a sampling component of a biopsy device engages the target tissue. In this embodiment, the sampling component comprises a coring component configured to penetrate a target tissue and to extract a tissue sample from the target tissue. At block 330 the biopsy device is anchored or secured to the target tissue by, for example, an anchoring element. The device may be secured to the target tissue to ensure that a desired portion of the target tissue is sampled by the coring component.

Following anchoring of the biopsy device to the target tissue, at block 332 the coring component penetrates the target tissue. As detailed further below, a surgeon may operate the biopsy device so as to cause the distal end of the coring component to penetrate the target tissue.

FIG. 3D is a flowchart illustrating certain other embodiments of block 320 of FIG. 3B in which a coring component is engaged with the target tissue. In the embodiments illustrated in FIG. 3C, the biopsy device includes an anchoring element in the form of an extendible anchor. As described in more detail below, in alternative embodiments the anchoring element may be attached to, or comprise part of the coring component. In certain embodiments, the anchoring element may comprise the coring component itself that is extended out a controlled distance. As shown, at block 340 the anchor may be extended from the biopsy device to the target tissue. In accordance with embodiments discussed below, at block 342 at least a portion of the anchor is secured or affixed to the target tissue.

After the anchor is secured to the target tissue, the coring component is extended to target tissue at block 344. At block 346, the coring component penetrates the target tissue such that a portion of the target tissue having a cross-section defined by the distal end of the coring component is received within the coring component.

As noted above with reference to block 302 of FIG. 3A, a distal end of the sampling component is positioned adjacent the target tissue prior to obtaining a sample of the target tissue. A biopsy device in accordance with embodiments of the present disclosure may include a variety of mechanisms or elements which permit a surgeon to guide the distal end of the sampling component to a desired location adjacent the target tissue. FIGS. 4A and 4B illustrate particular optional embodiments of a navigation tool 100 in which a navigation catheter 102 is used to guide the sampling component to a desired location.

In the embodiments of FIGS. 4A and 4B, navigation tool 100 includes a navigation catheter 102 having a proximal end 422 and a distal end 420, a handle 410 connected to the proximal end 422 of the navigation catheter 102 and a handle base 430. Handle 410 contains a lumen operationally contiguous with the lumen of navigation catheter 102 to allow for a biopsy catheter 436 to be inserted through navigation catheter 102. In embodiments, biopsy catheter 436 is connected to a control handle 434 to allow for manual rotation and extension of biopsy catheter 436 through navigation catheter 102. Alternatively, or additionally handle 434 may mate with handle 410, such that rotation and translation of handle 410 affects the movement of the biopsy catheter 436. As would be appreciated, handle 410 may include a variety of functional components.

In one embodiment of FIGS. 4A and 4B, handle 410 provides a surgeon with the ability to guide a sampling component (not shown) at the distal end of the biopsy catheter 436 such that a distal end of the sampling component is adjacent the target tissue by translating the handle 410 and the navigation catheter 102 longitudinally. In addition the handle 410 may be rotatable with respect to the handle base 430. This may be particularly useful in a luminal network having multiple branches such as the airways of the lungs. In such an embodiment the deflection of distal end 420 may be fixed during manufacture of navigation catheter 102. In such embodiments, a distal region of the navigation catheter 102 has a fixed radius of curvature. The location of distal end 420 may be controlled by rotation of handle 410 and advancement of the handle 410 over handle body 430 causing navigation catheter 102 to advance as well. In some embodiments, an adjustable stiffening stylet (not shown) can be inserted into a navigation catheter having a fixed curvature. The stylet has a fairly ridged structure so as it is inserted into the navigation catheter, the fixed radius of curvature of the navigation catheter can be reduced to nearly straight. As the stylet is retracted, the navigation catheter returns to its previous fixed radius of curvature. The biopsy catheter 436 may act as the stylet, such that advancement or retraction of the biopsy catheter 436 affects the curvature of the navigation catheter 102 which can aid in navigation of the navigation catheter 102 through bifurcations in the airways and other luminal networks where a single radius of curvature may result in navigational challenges.

In an alternative embodiment, handle 410 may include an articulation control section 432 and one or more wires (not shown). In the illustrated embodiment, articulation control section 432 is positioned between handle 410 and proximal end 422 of navigation catheter 102. The one or more wires extend from control section 432 through navigation catheter 102 to distal end 420 of navigation catheter 102. In one illustrated embodiment of the present disclosure, actuation of control section 432 exerts a push or pull force on one or more of the wires extending between control section 432 and distal end 420 of navigation catheter 102. The push or pull forces on the wires cause distal end 420 of navigation catheter 420 to deflect at one or more angles. In some embodiments, the use of more than one wire may allow for deflection in multiple planes (e.g. two or three dimensions).

As shown in FIG. 4A, control section 432 is positioned in a first configuration and distal end of navigation catheter 102 is substantially aligned with a longitudinal axis 440 of body 410. As shown in FIG. 4B, control section 432 is actuated by movement a distance 412 along axis 440 in the direction of body 410. Actuation of control section 432 causes distal end 420 to deflect a distance from longitudinal axis 440. In these embodiments, the magnitude of the deflection of distal end 420 may be controlled by the magnitude of the movement of moving control section 432.

As noted, in the embodiments illustrated in FIGS. 4A and 4B, control section 432 is configured to slide along axis 440 to exert push or pull forces on the wires extending to distal end 420. However, it should be appreciated that control section 432 may be actuated in a variety of manners. For example, in certain embodiments control section 432 may comprise a knob configured to be rotated in or more directions. In these embodiments, the magnitude of the deflection of distal end 420 is controlled by the rotation of the knob by the surgeon. In still other embodiments, control section 432 comprises a dual deflection control. The use of a dual deflection control would decrease the need to rotate the entire navigation tool 100. As would be appreciated by one of ordinary skill in the art, any conventional mechanism that uses a push/pull, twist, rotation or other similar motion to actuate, deflect and/or steer distal end 420 may be used in accordance with embodiments of the present disclosure.

In alternative embodiments of the present disclosure, articulation elements 432 may be omitted. As would be appreciated, endoscope body 410 may include a variety of functional components. In these embodiments, the magnitude of the deflection of distal end 420 may be controlled by, for example, a surgeon prior to insertion of navigation catheter 102 into the patient. In these embodiments, the surgeon may manually set the magnitude of deflection of distal end 420. In these embodiments, at least a distal region of navigation catheter 102 comprises a material that is flexible enough to be manually curved by the surgeon to a desired angle, but which has sufficient strength to maintain the desired angle during the biopsy procedure.

In further embodiments of FIGS. 4A and 4B, magnetic fields may be used to control the deflection of distal end 420. More specifically, internal magnets incorporated into navigation tool 100, and external magnets may be used to control the deflection of distal end 420 by pulling or pushing the distal end to the correct location.

In additional embodiments, shape memory materials may be used to cause a deflection of distal end 420. In these embodiments, upon the occurrence of a predetermined condition, the shape memory material causes distal end 420 to adopt a desired configuration. For example, in certain embodiments, shape memory wires may be included in navigation catheter 102. In embodiments, two or more shape memory components may be used to allow for more complex curvature and tissue targeting. In such embodiments, the length of the shape memory wires may be controlled so as to selectively extend navigation catheter 102. For example, the length of such shape memory wires may be lengthened or shortened by temperature changes. These temperature changes can be induced electrically, electronically, mechanically, hydraulically, conductively, inductively, radiantly, or by other known methods. This shortening and lengthening of the wire will create similar push/pull action as push/pull wires. The material for the shape memory component may be metal or polymer consisting of Nitinol or other shape memory metals or polymers.

In further embodiments, the distal region of navigation catheter 102 may comprise a shape memory material. In these embodiments, distal end 420 has a first configuration prior to insertion into a patient. Following insertion of navigation catheter 102, distal end 420 adopts a second configuration. As would be appreciated by one of ordinary skill in the art, distal end 420 may adopt the second configuration in response to, for example, a change in temperature or application of an electrical current thereto.

Furthermore, although FIGS. 4A and 4B have been described with reference to deflection of a distal end 420, it should be appreciated that any other methods now know or later developed for guiding or steering a sampling component to a location adjacent the target tissue are also within the scope of the present disclosure. It should also be appreciated that use of a navigation catheter 102 in embodiments of the present disclosure is optional and not required. For example, in certain embodiments a guide wire may be introduced into the patient and used by a surgeon to guide the sampling component to a location adjacent the target tissue.

Figure 5:
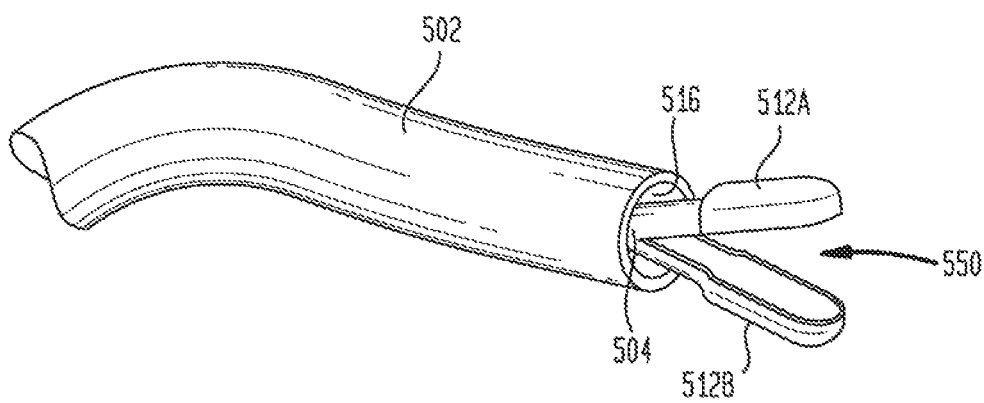
FIG. 5 is a perspective view of a biopsy device having a jaws arrangement for sampling a target tissue within a patient in accordance with embodiments of the present disclosure.

FIG. 5 is a perspective view of a distal region of a biopsy device 500 in accordance with particular embodiments of the present disclosure. As shown in FIG. 5, biopsy device 500 comprises a navigation catheter 502 having a lumen 516 there through. Extending through lumen 516 is a biopsy catheter 504 having an integrated sampling component 550 disposed at the distal end thereof configured to obtain a sample of a target tissue.

In the illustrated embodiment, sampling component 550 comprises a pair of opposing jaws 512 configured to be positioned around a portion of the target tissue, referred to herein as a tissue sample. Following positioning of opposing jaws 512 around the tissue sample, the surgeon may actuate jaws 512 so as to close the jaws about the tissue sample. In certain embodiments, jaws 512 may have sharpened, serrated or other edges such that closure of jaws 512 substantially severs the tissue sample from the remainder of the target tissue. As would be appreciated by one of ordinary skill in the art, biopsy device 500 may include various components which permit a surgeon to open and/or close jaws 512.

Figure 6:
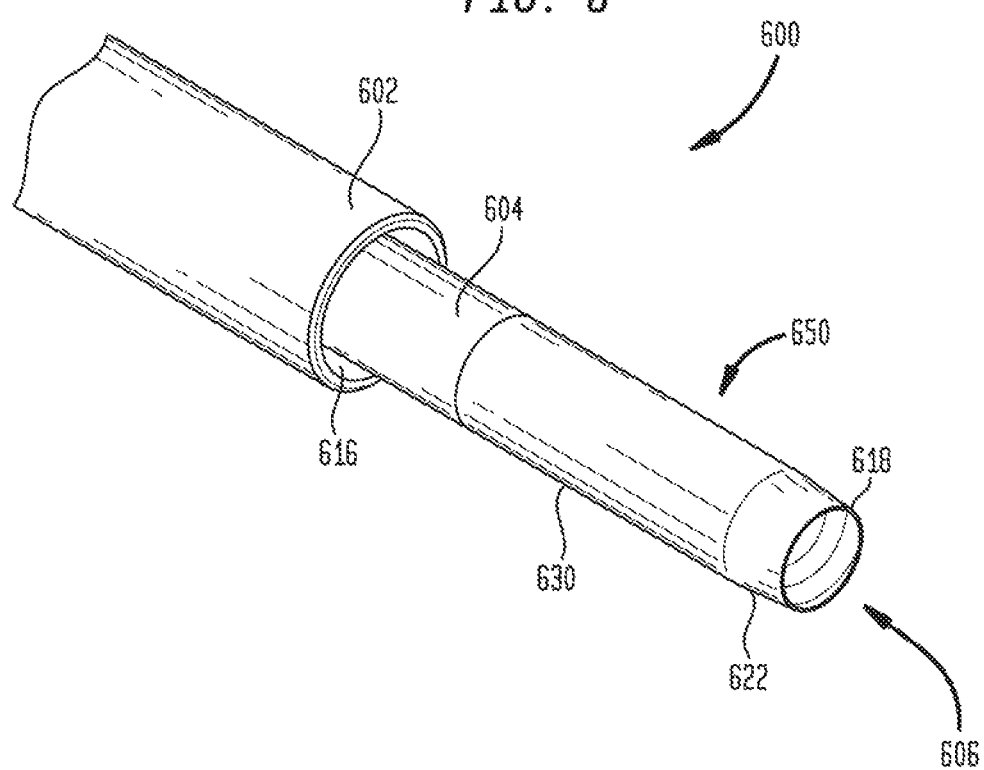
FIG. 6 is a perspective view of a biopsy device having a coring component for sampling a target tissue within a patient in accordance with embodiments of the present disclosure.

FIG. 6 is a perspective view of a distal region of a biopsy device 600 in accordance with embodiments of the present disclosure. Biopsy device 600 is configured to engage target tissue within a patient and to remove a sample of the target tissue from the patient.

As shown in FIG. 6, biopsy device 600 comprises a navigation catheter 602 having a biopsy catheter 604 extending there through. An integrated coring component 650 is disposed at the distal end of biopsy catheter 604 to sample a target tissue. Biopsy catheter 604 can be made of a flexible material. Coring component 650 comprises a longitudinal lumen terminating in a distal opening 606. The lumen of coring component 650 is operationally contiguous with the lumen of biopsy catheter 604. Coring component 650 may be formed from a tube and may be continuous around the circumference, as shown in FIG. 6, or be only portions of a circumference. Additionally, the distal end of coring component 650 can be chamfered or filleted for a sharper cutting edge and may vary in length.

A proximal region of coring component 650, shown as shaft 630, is permanently or removably connected to the distal end of biopsy catheter 604, and a distal region of the coring component is formed of one or more of a distally extending blade arrangement 622 each having a distal end positioned around distal opening 606. The blades are configured to penetrate the target tissue such that a tissue sample having a cross-section defined by the distal ends of the one or more blades is received within the lumen of coring component 650 via distal opening 606. The blades are configured to substantially sever the tissue sample from the remainder of the target tissue.

In the embodiments illustrated in FIG. 6, the distal region of coring component 650 is formed as a blade arrangement 622. Blade arrangement 622 has one or more cutting edges 618 positioned around distal opening 606 of coring component 650. In other embodiments, the interior surface of coring component 650 may further include a retention feature similar to retention feature 768 (shown in FIG. 7A) to assist in the extraction of the tissue sample. Blade arrangement 622 penetrates the target tissue such that a portion of the target tissue having a cross-section defined by the distal end of blade arrangement 622 is received within the lumen of coring component 650 via distal opening 606. The portion of the target tissue received within coring component 650 is referred to herein as a tissue sample. As described in more detail below, blade arrangement 622 is configured to substantially sever the tissue sample from the remainder of the target tissue.

As shown in FIG. 6, blade arrangement 622 has a single cutting edge substantially surrounding opening 606. FIGS. 7A through 7G illustrate other embodiments of coring components in accordance with embodiments of the present disclosure.

As noted above, a surgeon positions coring component 650 at a location such that the distal end of the coring component is adjacent the target tissue. Coring component 650 is extended to the target tissue and engaged therewith. As would be appreciated by one of ordinary skill in the art, biopsy device 600 may include various components which permit a surgeon to extend coring component 650 to the target tissue such as those described above in connection with FIGS. 4A and 4B.

As noted above, blade arrangement 622 is configured to penetrate the target tissue such that a portion of the target tissue having a cross-section defined the distal end of blade arrangement 622 is received within the lumen of coring component 650 via distal opening 606.

In certain embodiments of the present disclosure, blade arrangement 622 penetrates the target tissue in response to one or both of a longitudinal force exerted on the coring component 650 in the direction of the target tissue or a rotational force exerted on coring component 650. These rotational and/or longitudinal forces on coring component 650 may be applied in a variety of manners. For example, in certain embodiments, a surgeon may manually apply a longitudinal or rotational force. In other embodiments, biopsy device 600 may comprise any known articulation mechanism or element that permits a surgeon to apply the desired longitudinal or rotational force. In embodiments, biopsy device 600 may penetrate as much as 15 mm into the target tissue to obtain a tissue sample.

Also as noted above, blade arrangement 622 is configured to substantially sever the tissue sample from the remainder of the target tissue so that tissue sample suitable for proper examination is obtained during the sampling procedure. As noted above, certain sampling devices are unable to obtain large enough samples suitable for all types of examination. Blade arrangement 622 may sever the tissue sample in a variety of manners. In the specific embodiment of FIG. 6, blade arrangement 622 substantially severs the portion of target tissue positioned within coring component 650 via, for example, rotation of coring component 650 about a longitudinal axis extending through opening 606. As described below in more detail with reference to FIGS. 7A-7G, coring component 650 may be rotated manually by a surgeon or through the use of one or more elements included within biopsy device 600.

As explained above with reference to FIG. 3B, after the tissue sample has been substantially severed from the remainder of the target tissue, the tissue sample may be extracted from the target tissue by removing coring component 650 from the target tissue. Because, in certain embodiments, blade arrangement 622 substantially severs the tissue sample, the tissue sample may remain partially attached to the remainder of the target tissue. As discussed below in more detail, coring component 650 is configured to firmly secure the tissue sample such that removal of coring component 650 causes the tissue sample to become completely detached from the remainder of the target tissue.

As noted, in embodiments of the present disclosure, a lumen extends through biopsy catheter 604 that is operationally contiguous with a lumen of coring component 650. The operational contiguity of the lumens allows a surgeon to use the lumen during the biopsy procedure. For example, in certain embodiments, various devices may be inserted through the contiguous lumens such as optical devices, probes, forceps, needles, brushes, etc. Furthermore, the contiguous lumens permit a surgeon to deliver various treatments there through, before, during or after the obtaining the tissue sample.

FIGS. 7A-7D are perspective views of different embodiments of a coring component 750A-D in accordance with particular embodiments of FIG. 6. Since coring components 750A-D are configured in similar manners as coring component 650, the various configuration described above with reference to coring component 650 and FIG. 6 are also applicable to the coring components 750A-D described below with reference to FIGS. 7A-7D.

Figure 7A:
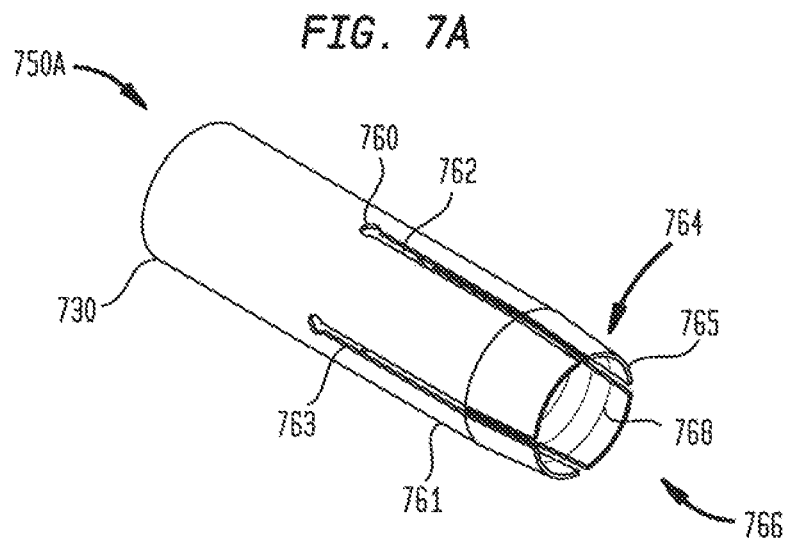
FIG. 7A is a front perspective view of a coring component in accordance with one embodiment of the present disclosure.

FIG. 7A is a front perspective view of a coring component 750A in accordance with particular embodiments of FIG. 6. As shown in FIG. 7A, coring component 750A comprises an elongate element having longitudinal lumen terminating in a distal opening 766. A distal region of coring component 750A is formed of a blade arrangement 764.

As shown in FIG. 7A, blade arrangement 764 comprises an elongate shaft 730 and plurality of distally extending blades 761 having their distal ends positioned around opening 766 of coring component 750A. In some embodiments, the distal ends of blades 761 are radially positioned around opening 766. The distal end of each blade 761 is a cutting edge 765. As shown in FIG. 7A, blade arrangement 764 comprises four blades 761. However, it should be appreciated that blade arrangement 764 may comprise more or fewer blades 761.

In the embodiments illustrated in FIGS. 7A-7D, each of the blades 761, 770, 780 have an approximately lunate cross-section. In other embodiments, each of the blades 761, 770, 780 have a cross-section of other geometries or shapes. Likewise in embodiments of the present, the cross-sections of each blades are not uniform.

In the same or other embodiments, blade arrangement 764 may substantially sever the tissue sample via closure of blades 761 to obtain a tissue sample suitable for proper examination. In the illustrated embodiments, at least one blade 761 is configured to flex inwardly towards a longitudinal axis extending through coring component 750A. The inward flexing of one or more blades 761 causes blades 761 to cut through the target tissue positioned there between so as to substantially sever the tissue sample from the remainder of the target tissue. These embodiments are described below in more detail with reference to FIGS. 8A and 8B.

In certain embodiments of FIG. 7A, each blade 761 is separated from adjacent blades by an elongate slit 762. Elongate slit 762 extends from opening 766 to a substantially circular aperture 760. Aperture 760 may enhance the inward flexing of one or more blades 761 during penetration of blades 761. In certain embodiments of the present disclosure, the tissue sample may be substantially severed from the target tissue via a combination of inward flexing of one or more blades 761 and rotation of coring component 750A.

As explained above with reference to FIG. 2B, following substantial severing of the tissue sample, the tissue sample is extracted from the target tissue by removing coring component 750A from the target tissue. In certain embodiments, blade arrangement 764 may firmly secure the tissue sample so as to permit detachment of the tissue sample from the remainder of the target tissue. In other embodiments, as shown in FIG. 7A, coring component 750A may further include a retention feature 768 to assist in the extraction of the tissue sample. In these embodiments, following penetration of blade arrangement 764 into the target tissue, retention feature 768 secures the tissue sample within the lumen of coring component 750A. During removal of coring component 750A from the target tissue, retention feature 768 remains secured to the tissue sample, thereby exerting an additional force on the tissue sample and further ensuring that the tissue sample is fully detached from the remainder of the target tissue. Tissue retention feature 768 has the further advantage of substantially preventing the tissue sample from being detached from the device during removal of the device from the patient.

In the illustrated embodiment of FIG. 7A, retention feature 768 may comprise a textured surface 768 of at least a portion of blade arrangement 764. More specifically, textured surface 768 may comprise a textured portion of a surface of one or more blades 761 adjacent the lumen of coring component 750A. In these embodiments, textured surface 768 attaches to the tissue sample and assists in securing the tissue sample within coring component 750A.

Various embodiments of retention feature 768 are within the scope of the present disclosure. For example, in one exemplary embodiment, retention feature 768 may comprise an adhesive applied to at least a portion of blade arrangement 768. In these embodiments, the adhesive has an adhesive force configured to secure tissue sample within coring component 750A, but which may be overcome by a surgeon with sufficient manual force following removal of coring component 750A from the patient. In these embodiments, retention feature 768 may comprise a reusable adhesive, such as a Gecko-Mussel adhesive.

In further embodiments, retention feature 768 may comprise a suction system included in the biopsy device configured to provide suction at or near coring component 750A. For example, in one such embodiment, suction may be provided through the lumen of coring component 750A to exert a force on the tissue sample and to assist in retaining the tissue sample therein. In other embodiments, suction may be provided around coring component 750A. Embodiments in which suction may be provided are described in more detail below with reference to FIGS. 13A-13C and FIG. 14.

In other embodiments, retention feature 768 may comprise one or more additional elements at or in coring component 750A. For example, in one such embodiment, retention feature 768 may comprise a needle positioned within coring component 750A to secure the tissue sample within the lumen of coring component 750A. These embodiments are described below in more detail with reference to FIGS. 11A and 11B. In still other embodiments, retention feature 768 may comprise one or more barbs, hooks, spikes, etc. provided on blade arrangement 764.

In other such embodiments, retention feature 768 may comprise a pair of opposing jaws. In these embodiments, opposing jaws are positioned within coring component 750A and are configured to secure the tissue sample within coring component 750A by attaching to at least a portion of the tissue sample. These embodiments are described below in more detail with reference to FIGS. 10A and 10B.

Furthermore, as noted above, each blade 761 includes cutting edges 765 disposed at the distal end there of blades 761. It should be appreciated that each blade 761 may also include additional cutting edges. For example, each blade may include one or more longitudinally extending cutting edges 763.

The configurations described above with reference to FIG. 6 can also be equally applied to coring components described in FIGS. 7A-7D. In particular, the methods of tissue retention, severing, and extraction described above with reference to coring component 760 may also be applicable to coring component 770, 780, 790.

Figure 7B:
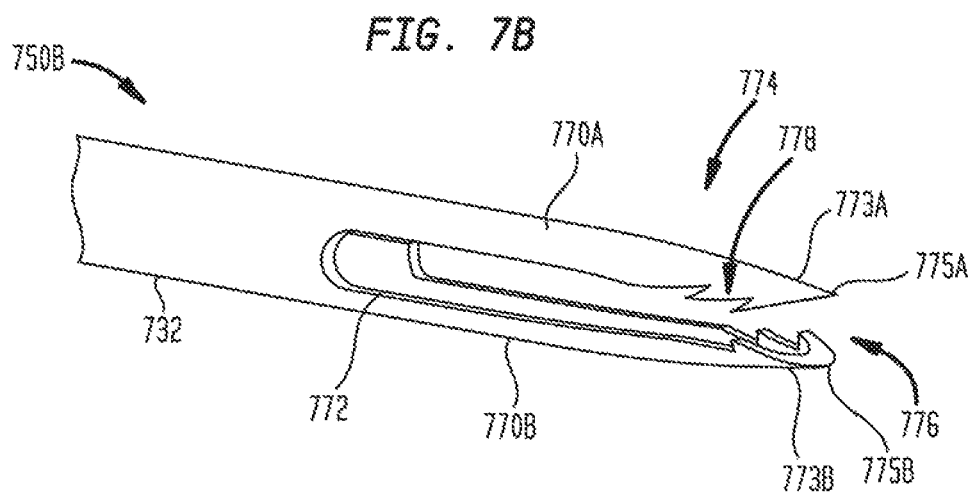
FIG. 7B is a perspective view of a coring component in accordance with one embodiment of the present disclosure.

FIG. 7B is a perspective view of a coring component 750B in accordance with certain embodiments of FIG. 5. As shown in FIG. 7B, coring component 750B comprises an elongate element having a longitudinal lumen terminating in a distal opening 776. A distal region of coring component 732 is formed of a blade arrangement 774.

As shown in FIG. 7B, blade arrangement 774 comprises a plurality of distally extending blades 770A, 770B comprising cutting edges 775 having their distal ends positioned around distal opening 776 of coring component 750B. In the illustrated embodiment, each blade 770 has an approximately lunate cross-section. In other embodiments, each blade 770 has a cross-section of other geometries or shapes.

As described above with reference to FIGS. 6 and 7A, blade arrangement 774 is configured to penetrate the target tissue such that a portion of the target tissue having a cross-section defined by the distal end of blade arrangement 774 is received within the lumen of coring component 750B via distal opening 766.

Blade arrangement 774 may substantially sever the tissue sample from the target tissue in a variety of manners. For example, in certain embodiments, coring component 750B is configured to be rotatable with respect to the target tissue. In response to the rotation of coring component 750B, cutting edges 775 of blades 770 substantially reduce the cross-sectional diameter of the portion of the target tissue positioned there between proximate to distal opening 776.

In the same or other embodiments, blade arrangement 774 may substantially sever the tissue sample via closure of blades 770. In these embodiments, at least one blade 770 is configured to flex inwardly towards a longitudinal of coring component 750B. The inward flexing of one or more blades 770 causes blades 770 to cut through the target tissue positioned there between so as to substantially sever the tissue sample from the remainder of the target tissue. These embodiments are described below in more detail with reference to FIGS. 8A and 8B.

As shown in FIG. 7B, retention feature 778 comprises a plurality of barbs 778 positioned on the surface of blades 770 adjacent the lumen of coring component 750B. In these embodiments, following penetration of blades 770 into the target tissue, barbs 778 attach to the tissue sample. When the surgeon removes coring component 750B from the target tissue, barbs 778 exert a force on the tissue sample to retain the tissue sample within coring component 750B. Although FIG. 7B has been described with reference to barbs 778, it should be appreciated that other retention features may also be used with coring component 750B similar to those described above with reference to FIG. 7A.

In the illustrated embodiments, each blade 770 includes cutting edges 775 disposed at the distal end there of blades 770. It should be appreciated that each blade 770 may also include additional cutting edges. For example, each blade may include one or more longitudinally extending cutting edges 772.

In particular embodiments blades 770 are configured to flex inwardly during penetration of the target tissue. In certain such embodiments, blades 770 each comprise a curved or beveled surface 773A, 773B (generally and collectively referred to as a "beveled surface" herein) that help push blades 770 inward upon penetration. As blades 770 are inserted into the target tissue, the target tissue adjoining beveled surfaces 773A, 773B exert a force on the beveled surfaces pushing the blades 770 inward. This force exerted by the target tissue on beveled surfaces 773A, 773B increases as blades 770 penetrate deeper into the target tissue.

Figure 7C:
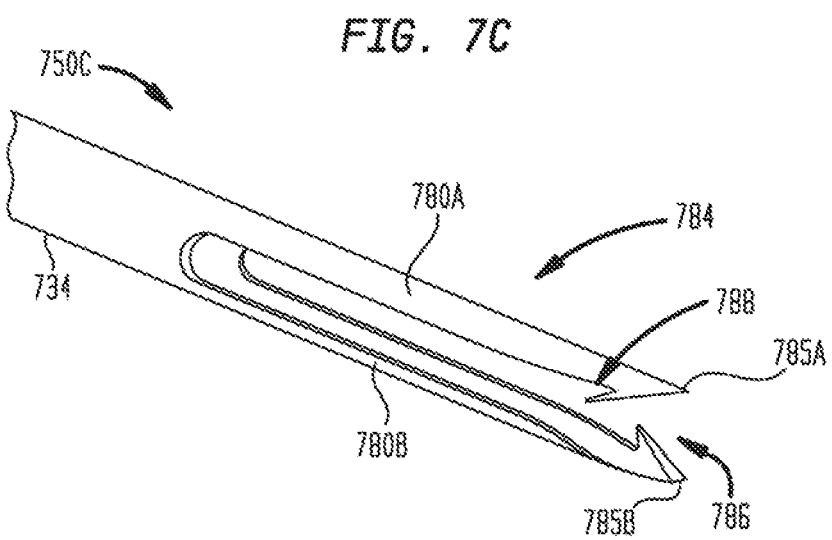
FIG. 7C is a perspective view of a coring component in accordance with one embodiment of the present disclosure.

FIG. 7C is a perspective view of a coring component 750C. As shown in FIG. 7C, coring component 750C comprises an elongate element having a longitudinal lumen terminating in a distal opening 786. A distal region of coring component 750C is formed of a blade arrangement 784.

As shown in FIG. 7C, blade arrangement 784 comprises a plurality of distally extending blades 780A, 780B having their distal ends positioned around distal opening 786 of coring component 750C. The distal end of each blade 780A, B is a cutting edge 785A, B. As shown in FIG. 7C, blade arrangement 784 comprises a pair of opposing blades 780. However, it should be appreciated that blade arrangement 780 may comprise more or less blades 780. In embodiments, the blades 780A, 780B expand radially when pushed against tissue during biopsy penetration. This can result in an inward radial force that helps retain the tissue sample. Additionally, barbs 788 can help retain tissue. When the blades 780A, 780B radially expand during penetration, the blades 780A, 780B can be manually constricted by advancing an outer navigation catheter having a reduced diameter, relative to the expanded blades 780A, 780B, forward and over the blades 780A, 780B to bring them radially inward to constrict and retain the tissue sample.

Since blade arrangement 784 is similar to blade arrangement 774, the configurations described above with reference to FIG. 7A can also be equally applied to blade arrangement 784 described in FIG. 7C. In particular, the methods of tissue retention, severing, and extraction described above with reference to coring component 770 may also be applicable to coring component 780.

Figure 7D:
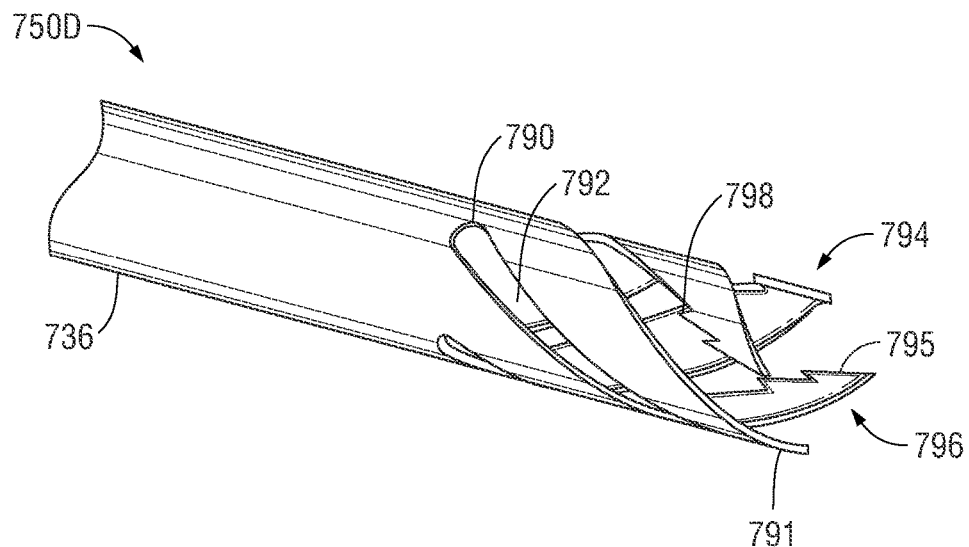
FIG. 7D is a perspective view of a coring component in accordance with one embodiment of the present disclosure.

7D is a perspective view of a coring component 750D in accordance with certain embodiments of FIG. 6. As shown in FIG. 7D, coring component 750D comprises an elongate element having a longitudinal lumen terminating in a distal opening 796. A distal region of coring component 750D is formed of a blade arrangement 794.

As shown in FIG. 7D, blade arrangement 794 comprises an elongate shaft 736 and a plurality of distally extending spiral blades 791 having their distal ends positioned around opening 796 of coring component 750D. In some embodiments, the distal ends of spiral blades 791 are radially positioned around opening 796. The exposed edges of each spiral blade 791 is a cutting edge 795. As shown in FIG. 7D, blade arrangement 794 comprises four spiral blades 791. However, it should be appreciated that blade arrangement 794 may comprise more or fewer spiral blades 791.

In certain embodiments of FIG. 7D, each blade 791 is separated from adjacent blades by an elongate slit 792. Elongate slit 792 extends from opening 796 to a substantially circular aperture 790. Aperture 790 may enhance the inward flexing of one or more blades 791 during penetration of blades 791.

In certain embodiments of FIG. 7D, the elongate slits 792 of the coring component 750D are configured so blades 791 move towards the longitudinal center of elongate shaft 736 when the coring component is retracted from target tissue. In this embodiment, coring component 750D functions similar to a Chinese finger puzzle. As the coring component 750D is retracted, the blades 791 reduce the diameter of elongate shaft 736 causing it to squeeze around and part-off the tissue sample. This part-off during retraction can be automatically triggered during retraction or manually activated by the operator. For example, the part-off may be manually activated through the use of one or more pull wire or by rotating the elongate shaft 736 and coring component 750D. Further, the blades 791 could be twisted (like blades of a propeller), such that a rotary motion would increase the blades 791 movement toward or away from the longitudinal center of elongate shaft 736, dependent on the relative twist angle (positive vs. negative) compared to the perimeter tangent angle of zero.

Figure 7E:
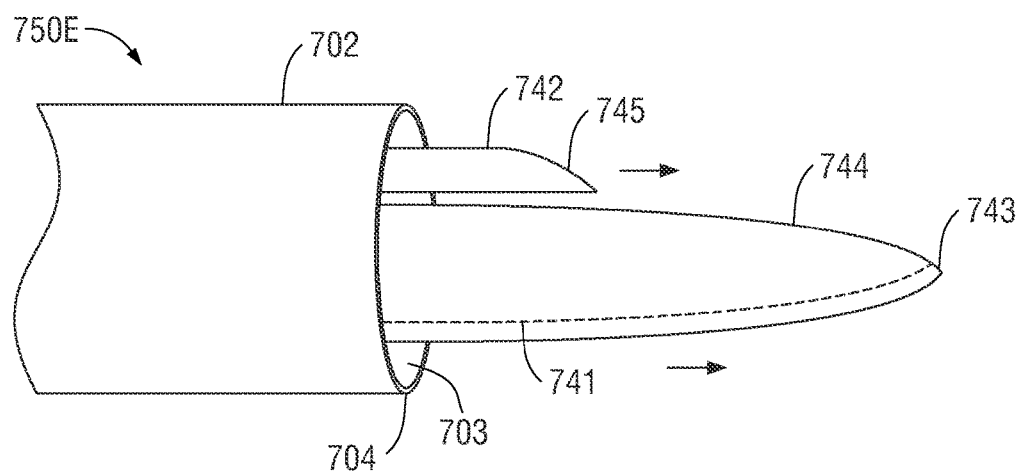
FIG. 7E is a front perspective view of a coring component having a first and second blade in accordance with one embodiment of the present disclosure.

FIG. 7E is a perspective view of another embodiment of a coring component 750E. As shown in FIG. 7E, coring component comprises a navigation catheter 702 having a lumen 703 there through. Extending through lumen 703 is a first blade 741 and a second blade 742 disposed at the distal end thereof and configured to core and part-off a tissue sample from a target tissue. In embodiments, the first blade 741 and second blade 742 are angle.

In the illustrated embodiment, first blade 741 has a distal end 743 and edge 744. In these embodiments, first blade 741 is configured to advance a small amount past the distal end 704 of catheter 702 to aid in placement and anchoring of the coring component 750E. In certain embodiments, distal end 743 of first blade 741 is pointed and/or comprises a needle like component to help anchor the first blade 741 to a target tissue. Once anchored, second blade 742 can then be advanced to the point of coring and/or parting-off of tissue sample. In embodiments, first blade 741 and second blade 742 both have edges 743, 745 may be sharp, serrated, and/or may be angled or barbed to allow for a more efficient parting-off or slicing of a tissue sample. Additionally, in some embodiments, only a portion of edge 743, 745 is sharp. As the second blade 742 is advanced and retracted, a portion of the tissue sample is severed. A surgeon continues this process of advancing and retracting the second blade 742 until enough of the tissue sample is severed from the target tissue.

In one embodiment, the second blade 742 is a needle. The needle comprises a lumen and a sharp end. As the second blade 742 is advanced and retracted, severed tissue sample is collected in the lumen. In this embodiment, the second blade 742 may be coupled to either a syringe or suction device that can retain or aspirate the tissue sample in order to extract the severed tissue sample. In other embodiments, the second blade 742 may be removed and the tissue sample may be manually extracted from the lumen by the surgeon.

As noted above, a surgeon positions coring component 750E at a location such that the distal end of the coring component is adjacent the target tissue. Coring component 750E is extended past the distal end 704 of catheter 702 to the target tissue and engaged therewith. As would be appreciated by one of ordinary skill in the art, coring component 750E, including first blade 741 and second blade 742, may include various components which permit a surgeon to extend coring component 750E to the target tissue. For example, in certain embodiments, first blade 741 and second blade 742 comprise one or more push/pull wires which allow a surgeon to selectively extend first blade 741 and second blade 742. Such push/pull wires may be controlled, for example, via by thumb knobs or various other mechanisms. In embodiments, the advancement of first blade 741 and second blade 742 can be controlled by a single handed device utilizing push/pull wires for easy control and manipulation by a surgeon. For example, the device may have a three-finger activation with a push/pull ring for a thumb, index finger, and middle finger. The device may also allow for incremental advancement of the first blade 741 and second blade 742. For example, a 1 mm advancement of the first blade 741 or second blade 742

In embodiments, suction may be provided around coring component 750E. Embodiments in which suction may be provided are described in more detail below with reference to FIGS. 13A-13C and 14.

In still other embodiments, retention feature may comprise one or more barbs or spikes provided on first blade 741 and/or second blade 742 similar to those embodiments discussed above with reference to FIGS. 6-7D.

In other embodiments, anchoring can be performed by providing for a coring component, as shown in FIGS. 7A-7E, with a textured surface. A textured, or roughened, surface can be created mechanically (e.g. machined, laser, blasting, abrasion, grinding, filing, molding, knurling, stamping, electron bombardment, etc.), chemically (e.g. etching, de alloy, pit, photolithography, plating etc.), or other common methods of surface roughening. Alternatively, a biocompatible adhesive can be applied to the coring component to help grip surface, for example Gecko-Mussel biomimetic which consists of hair-like hooks mixed with wet compatible adhesive.

Figure 7F:
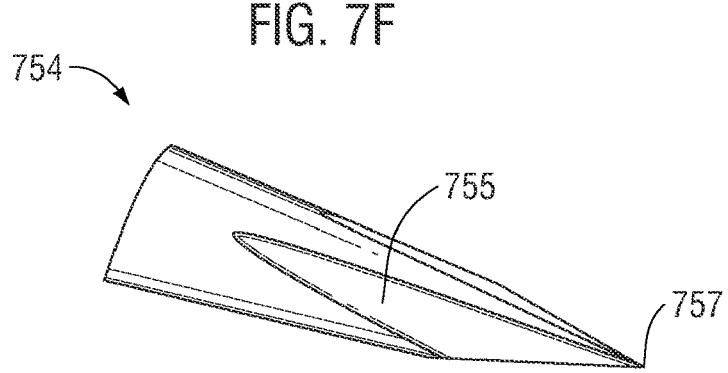
FIG. 7F is a perspective view of the outer surface of an embodiment of a blade arrangement.
Figure 7G:
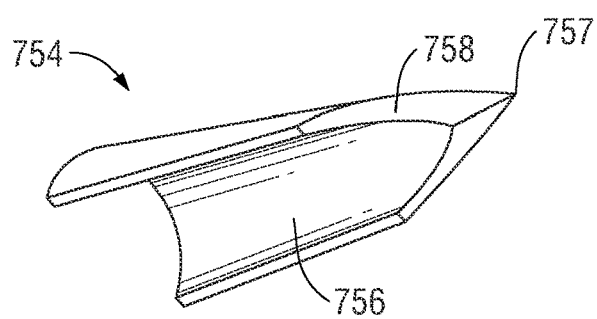
FIG. 7G is a perspective view of the outer surface of an embodiment of a blade arrangement.

FIGS. 7F and 7G are perspective views of alternative embodiments of blade arrangements described above with reference to FIGS. 7A-7E. In particular, blade arrangement 754 of FIGS. 7F and 7G illustrates different shapes of blade arrangements 764, 774, 784, 794, 741, 742. Blade arrangement 754 is comprises an outer surface 755, an inner surface 756, a pointed distal end 757, and a sharp edge 758.

Figure 7H:
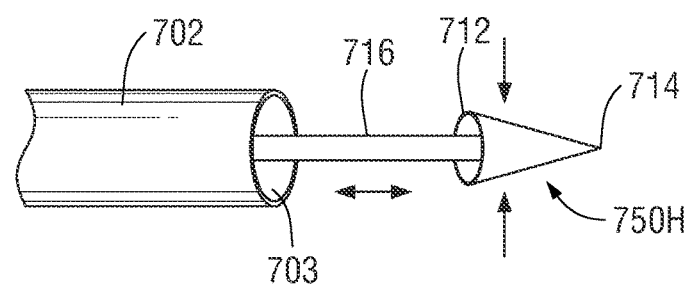
FIG. 7H is a perspective view of a coring component in accordance with one embodiment of the present disclosure.

FIG. 7H is a perspective view of another embodiment of a coring component 750H. As shown in FIG. 7H, coring component comprises a catheter 702 having a lumen 703 there through. Extending through lumen 703 is a biopsy catheter 716 having a coring component 750H at the distal end of the shaft. The coring component 750H has shape of a hollow cone 714 with an edge 712. The hollow cone 714 has a retractable profile (as shown by the arrows), which may be spring loaded or otherwise actuatable. The coring component 750H first pierces the target tissue with a reduced profile of the distal end of the hollow code 714. When the coring component 750H is retracted, the sharp edge 712 cuts a tissue sample from the target tissue and the entire coring component is retracted to retrieve the tissue sample. In embodiments, the tissue sample is retained in the hollow cone 714. In embodiments, the retractable profile of hollow cone 714 is controlled through a series of pull wires controlled by a surgeon. In a further embodiment, the coring component 750H is inserted into the target tissue in a folded shape, and following insertion the hollow cone 714 is opened to increase its profile.

Figure 8A:
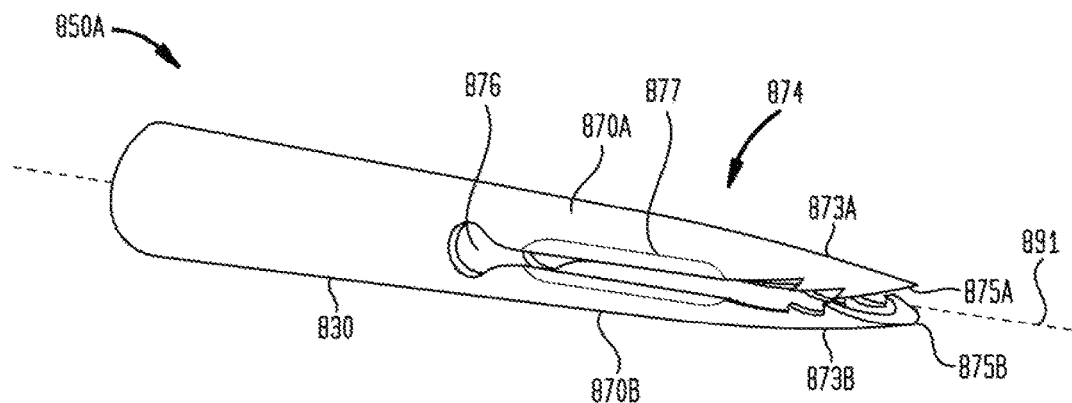
FIG. 8A is a perspective view of a coring component in accordance with one embodiment of the present disclosure.
Figure 8B:
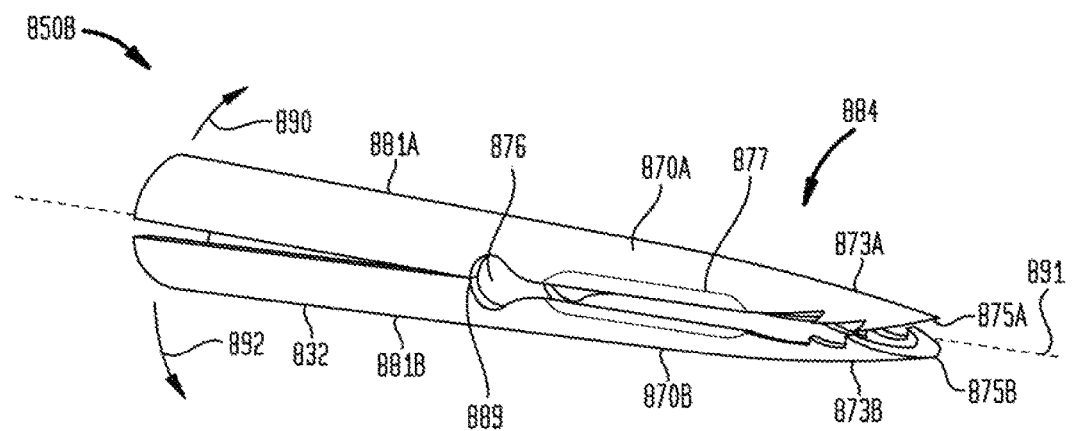
FIG. 8B is a perspective view of a coring component in accordance with one embodiment of the present disclosure.

FIGS. 8A and 8B are perspective views of embodiments of coring components 850 in accordance with certain embodiments of the present disclosure. In particular, FIGS. 8A and 8B illustrate embodiments of coring components 850 configured to sever a tissue sample via closure of elements of coring components 850.

Figure 8C:
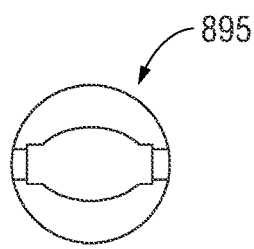
FIG. 8C is a cross-section view of a coring component as shown in FIGS. 8A and 8B.
Figure 9A:
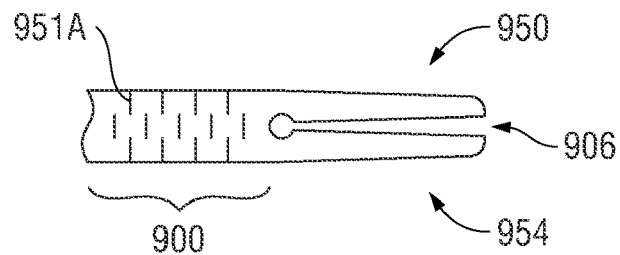
FIG. 9A is a perspective view of a biopsy device having slits in the proximal section of the biopsy component to aid in flexibility of the biopsy device in accordance with one embodiment of the present disclosure.
Figure 9B:
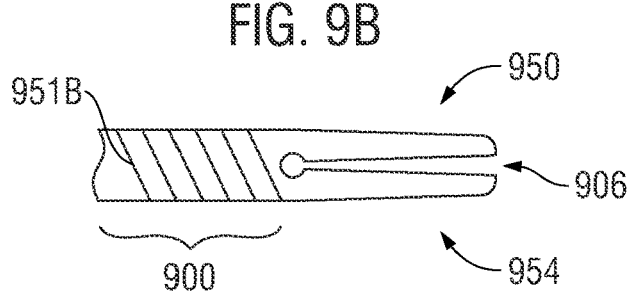
FIG. 9B is a perspective view of a biopsy device having slits in the proximal section of the biopsy component to aid in flexibility of the biopsy device in accordance with one embodiment of the present disclosure.
Figure 9C:
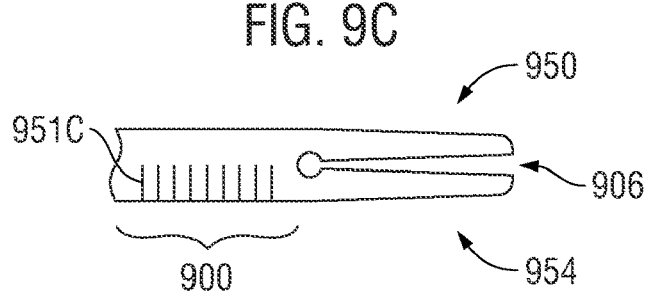
FIG. 9C is a perspective view of a biopsy device having slits in the proximal section of the biopsy component to aid in flexibility of the biopsy device in accordance with one embodiment of the present disclosure.
Figure 9D:
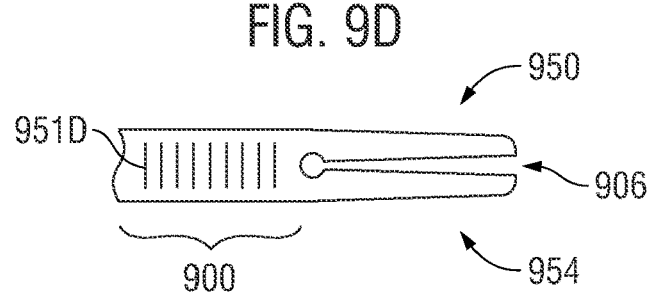
FIG. 9D is a perspective view of a biopsy device having slits in the proximal section of the biopsy component to aid in flexibility of the biopsy device in accordance with one embodiment of the present disclosure.

As shown in FIG. 8A-8C, coring component 850A comprises an elongate element 830 having a longitudinal lumen terminating in a distal opening. A distal region of element 830 is formed of a blade arrangement 874 having one or more cutting edges 875 positioned around the distal opening of coring component 850A. In the illustrated embodiment, blade arrangement 874 comprises a pair of opposing blades 870 each having an approximately lunate cross-section 895 (as shown in FIG. 8C) and a sharpened edge 877. In the embodiments of FIG. 8A, prior to penetration of blades 870 into the target tissue, the distal end of blades 870 are positioned around the distal opening of coring component 850A.

As discussed above with reference to FIG. 7B, blade arrangement 874 is configured to penetrate the target tissue such that a portion of the target tissue having a cross-section defined by an inner diameter of the distal end of blade arrangement 874 is received within the lumen of coring component 850A via the distal opening of coring component 850A. Also, as noted above, blade arrangement 874 is configured to substantially sever the portion of the target tissue received within coring component 850A, referred to as the tissue sample, from the remainder of the target tissue.

In the embodiments illustrated in FIG. 8A and 8B, blade arrangement 874 may substantially sever the tissue sample via closure of blades 870. In particular embodiments illustrated in FIG. 8A and 8B, blades 870 are configured to flex inwardly during penetration of the target tissue. In certain such embodiments, blades 870 each comprise a curved or beveled surface 873 (generally and collectively referred to as a "beveled surface" herein). As blades 870 are inserted into the target tissue, the target tissue adjoining beveled surfaces 873 exert a force on the beveled surfaces in the direction of longitudinal axis 891. This force exerted by the target tissue on beveled surfaces 873 increases as blades 870 penetrate deeper into the target tissue.

As the force on bevel surfaces 873 increase, the beveled surfaces are forced inwardly towards axis 891. Each blade has sufficient strength such that as beveled surfaces 873 flex towards axis 891, cutting edges of blades 870 cut through the target tissue. As shown in FIG. 8A, following penetration of blades 870 to a predetermined depth, the distal ends of blades 870 are positioned substantially adjacent axis 891.

In accordance with other embodiments illustrated in FIG. 8A and 8B, blades 870 are configured to flex inwards following penetration of the target tissue by blades 870. In one such embodiment, blades 870 comprise a shape memory material configured to flex inwardly toward axis 891 following insertion. Blades 870 may flex inwardly in response to, for example, a change in temperature induced by the target tissue. In another such embodiment, blades 870 may flex inwardly in response to application of an electrical current to blades 870.

The configurations described above with reference to FIGS. 6 and 7A-7G can also be equally applied to coring components described in FIGS. 8A and 8B. In particular, the methods of tissue retention, severing, and extraction described above can also be applied to the coring component of FIGS. 8A and 8B.

FIG. 8B illustrates an alternative coring component 850B in which a tissue portion received therein, referred to as the tissue sample, may be substantially severed via closure of blades 870 of coring component 850B. As shown in FIG. 8B, in certain embodiments coring component 850B comprises a two-piece component comprising opposing elements 881. Opposing elements 881 collectively define the longitudinal lumen extending there through. In the embodiments of FIG. 8B, elements 881 are connected to one another via a hinge arrangement 889. In certain embodiments, hinge arrangement 889 enhances the ability of blades 870 to flex inwards in response to forces on beveled surfaces 873 during penetration. In other embodiments, hinge arrangement 889 enhances the response of blades comprising shape memory materials to changes in temperature or to an electrical current.

In other embodiments, hinge arrangement 889 provides a surgeon with the ability to mechanically close blades 870. In certain embodiments, a biopsy device having coring component 850B therein includes a component which permits a surgeon to actuate hinge arrangement 889. Actuation of hinge arrangement 889 causes the distal ends of one or more of blades 870 to flex inwards towards axis 891. In such embodiments, the proximal ends 889 of elements 881 are forced away from axis 891, shown by directional arrows 890, 892. In embodiments of the present disclosure, the surgeon may actuate hinge mechanism during or following penetration of the target tissue by blades 870.

In another embodiment, coring components 850A, 850B may be electrically connected to a cauterizing controller and energy source and be configured to simultaneously cauterize the target tissue. Cauterizing can help aid in the cutting and coring process and help to stop any bleeding complications. The energy generating source may be any generator suitable for use with electrosurgical devices and capable of providing electrosurgical energy to monopolar or bipolar devices to cauterize tissue. Examples of electrosurgical generators that may be suitable for use as a source of electrosurgical energy are commercially available under the trademarks FORCE EZ™, FORCE FX™, and FORCE TRIAD™ offered by Covidien LP.

FIGS. 9A-9D are front perspective views of a coring component 950 in accordance with particular embodiments of FIGS. 6, 7A-7G, 8A, and 8B. As shown in FIGS. 9A-9D, coring component 950 comprises an elongate element having longitudinal lumen terminating in a distal opening 906. A distal region of coring component 950 is formed of a blade arrangement 954. As shown in FIGS. 9A-9D, alternative embodiments of coring component 950 may comprise of alternating slits 951A, spiral slits 951B, spine cuts 951C, or dual spine cuts 951D. Spiral slits 951B are made on an angle, for example a 45 degree angle, and are relatively parallel to each other. The spiral slits 951B allow the flexible proximal section 900 to flex in multiple directions and multiple planes. Spine cuts 951C provide for directional flexibility. The spine cuts 951C are made along one side of the coring component 950. Depending on which side the spine cuts 951C are positioned, the coring component 950 is able to flex towards the opposite direction. As shown, the spine cuts 951C are relatively parallel to each other, although this is not necessary. The dual spine cuts 951D are made along opposite sides of the coring component 950F. The dual spine cuts 951D allow coring component 950 to flex in a similar fashion as described above with reference to FIG. 9C, however in multiple directions. As shown, the dual spine cuts 957 are relatively parallel to each other, although this is not necessary.

The various slits 951A-D aid in flexibility and provide for good coupling of the coring component 950 while still helping to maintain adequate column strength and torqueability. In some embodiments, the entire circumference of the flexible proximal section 900 consists of one of more slits 951A-D, while in other embodiments, only a portion of the flexible proximal section 900 consists of one of more slits 951A-D. The slits 951A-D may range in length. For example, they may range from a length of 1 mm-1 cm, or alternatively, they may range in length from about one quarter the diameter or width of the coring component 950 to about three quarters the diameter or width of the coring component 950.

Although the distal region of coring component 950 depicts a blade arrangement 954, similar to that described above in FIG. 7C, alternative embodiments are imagined. In particular, coring component 950 and blade arrangement 954 may comprise of coring components consistent with those described above with reference to FIGS. 6, 7A-7G, 8A, and 8B.

Figure 10A:
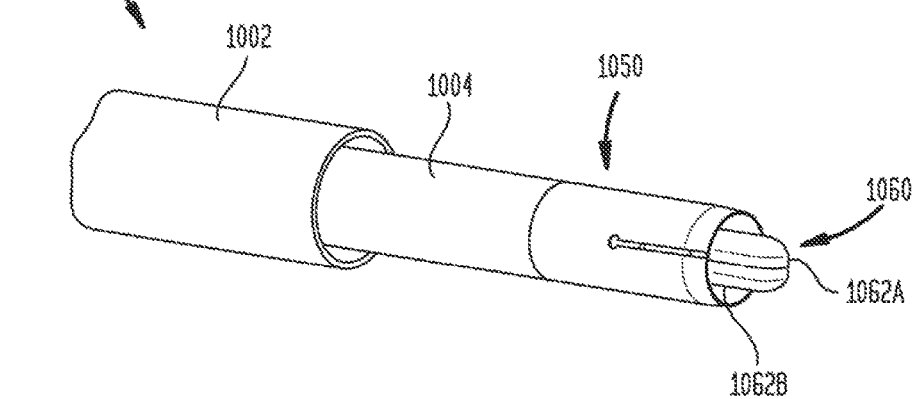
FIG. 10A is a perspective view of a biopsy device having an anchoring element in accordance with one embodiment of the present disclosure.
Figure 10B:
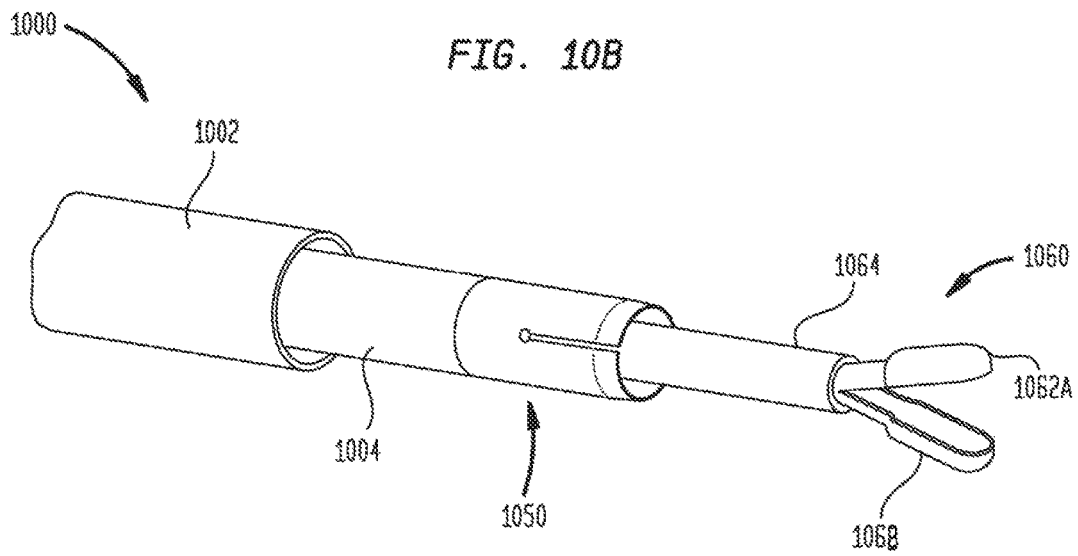
FIG. 10B is a perspective view of the embodiment of a biopsy device shown in FIG. 10A.

As noted above with reference to FIG. 3D, certain embodiments of the present disclosure may include an element configured to be controllably extended from the biopsy device to secure the biopsy device to the target tissue, referred to as an extendible anchoring element. FIGS. 10A and 10B are front perspective views of a distal region of an endoscopic biopsy device 1000 having such an extendible anchoring element, referred to as anchoring element 1060.

As noted above, an endoscopic biopsy device in accordance with embodiments of the present disclosure, such as biopsy device 1000, includes a navigation catheter 1002, a biopsy catheter 1004 and a sampling component 1050 positioned at the distal end of biopsy catheter 1004. In the illustrated embodiment, sampling component 1050 comprises a coring component 1050.

As shown below, anchoring element 1060 causes biopsy device 1000 to be located at the proper location prior to insertion of the coring component 1050 into the target tissue. Furthermore, anchoring element 1060 prevents coring component 1050 from slipping, sliding or moving relative to the target tissue immediately before or during penetration.

Similar to embodiments described above, biopsy device 1000 comprises a catheter 1002 having a lumen therethrough. Extending through the lumen is a biopsy catheter 1004 having a sampling component 1050 positioned at the distal end thereof. In the embodiments of FIGS. 10A and 10B, biopsy device 1000 comprises a coring component 1050.

FIG. 10A illustrates the configuration of biopsy device 1000 prior to extension of anchoring element 1060. FIG. 10B illustrates the configuration of biopsy device 1000 following extension of anchoring element 1060, but prior to extension of coring component 1050 to the target tissue.

As shown in FIG. 10A, in a first configuration anchoring element 1060 is positioned within coring component 1050. As noted above, in embodiments of the present disclosure, biopsy catheter 1004 and coring component 1050 have a lumen extending therein. As shown in FIGS. 10A and 10B, anchoring element 1060 may be positioned in this lumen.

Anchoring element 1060 comprises an elongate shaft 1064 and a pair of opposing jaws 1062. In these embodiments, a surgeon may extend anchoring element 1060 from with the lumen of coring component 1050 such that jaws 1062 contact the target tissue. Jaws 1062 may then be closed around a portion of the target tissue to secure biopsy device 1000 to the target tissue. In embodiments illustrated in FIGS. 10A and 10B, jaws 1062 close around a portion of the target tissue such that coring component 1050 may penetrate the target tissue around closed jaws 1062.

In certain embodiments of the present disclosure, jaws 1062 may release the target tissue during penetration of the target tissue by coring component 1050. In other embodiments of the present disclosure, jaws 1062 may remain attached to the target tissue during and following penetration of the component. As such, as described above with reference to FIGS. 6-7C, coring component 1050 is configured to substantially sever at least the portion of the target attached to jaws 1062. In these embodiments, because jaws 1062 remain attached to the severed tissue portion, jaws 1062 function as a retention feature to assist in the removal of the severed portion from the target tissue.

Although FIGS. 10A and 10B have been described herein with reference to a sampling component 1050 in the form of a coring component, it should would be appreciated that anchoring element 1060 comprising jaws 1062 may be used in conjunction with alternative sampling components. For example, in alternative embodiments of the present disclosure, a sampling component in the form of a jaws arrangement, such as the jaws arrangement described with reference to FIG. 5, may be used in conjunction with anchoring element 1060. In certain such embodiments, the anchoring element 1060 would be controllable extended from within the opposing jaws of the jaws arrangement. Furthermore, although anchoring element 1060 has been shown extending from within coring component 1050, it should be appreciated that anchoring may be extended from other locations as well, such as adjacent the coring component, around the coring component, etc.

Figure 11A:
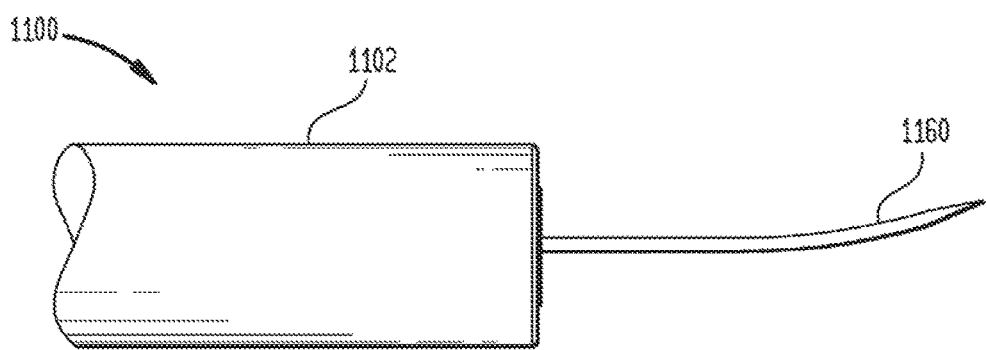
FIG. 11A is a side view of a biopsy device having an anchoring element in accordance with one embodiment of the present disclosure.
Figure 11B:
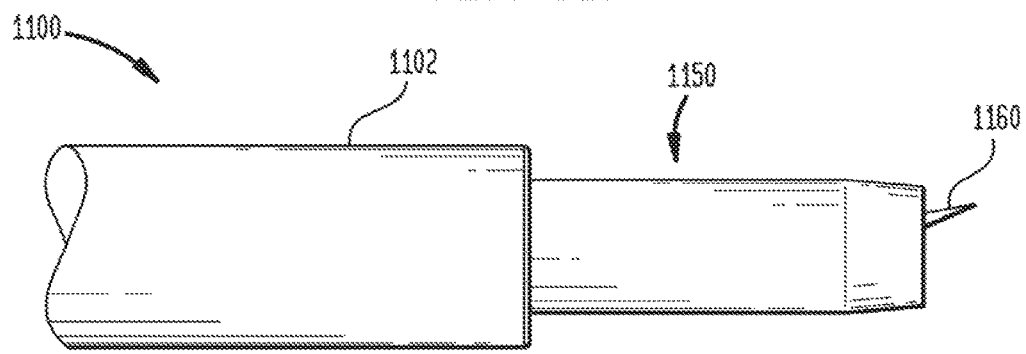
FIG. 11B is a side view of the embodiment of a biopsy device shown in FIG. 11A.

FIGS. 11A and 11B are side views of a distal region of embodiments of an endoscopic biopsy device 1100 having an extendible anchoring element, referred to as anchoring element 1160. Similar to embodiments described above, biopsy device 1100 comprises a navigation catheter 1102 having a lumen there through. Extending through the lumen is a catheter (not shown) having a sampling component 1150 positioned at the distal end thereof. In the embodiments of FIGS. 11A and 11B, biopsy device 1100 comprises a coring component 1150.

FIG. 11A illustrates the configuration of biopsy device 1100 following extension of anchoring element 1160, but prior to extension of coring component 1150. FIG. 11B illustrates the configuration of biopsy device 1100 following extension anchoring element 1160 and of coring component 1150. As shown, anchoring element 1160 comprises a bent or hooked needle 1160. In these embodiments, a surgeon may extend needle 1160 from within coring component 1150 such that needle 1160 penetrates a portion of the target tissue and remains secured therein. In embodiments of the present disclosure, coring component 1150 penetrates the target tissue around needle 1160.

In certain embodiments of the present disclosure, needle 1160 may be removed from the target tissue during penetration of the target tissue by coring component 1150. In other embodiments of the present disclosure, needle 1160 may remain attached to the target tissue during and following penetration of the component due to its bent or hooked configuration. In such embodiments, coring component 1150 penetrates the target tissue around needle 1160. As such, as described above with reference to FIGS. 6-7C, coring component 1150 is configured to substantially sever at least the portion of the target tissue attached to needle 1160. In these embodiments, because needle 1160 remains attached to the severed tissue portion due to its bent or hooked configuration, needle 1160 functions as a retention feature to assist in the removal of the severed portion from the target tissue.

In the embodiments illustrated in FIGS. 11A and 11B, the distal end of needle 1160 is curved. However, it should be appreciated that other configurations for needle 1160 are within the scope of the present disclosure. For example, in certain embodiments, needle 1160 may be straight, corkscrewed, angled, have multiple angles, barbed, hooked, etc. Furthermore, FIGS. 11A and 11B illustrate the use of a single needle. However, it should also be appreciated that multiple extendible needles may also be used in substantially the same manner as described above. It should also be appreciated that in embodiments of the present disclosure, needle 1160 may be bent or straight, solid or hollow wire, and may be integrated or separate from any of navigation catheter 1102 and coring component 1150.

Figure 11C:
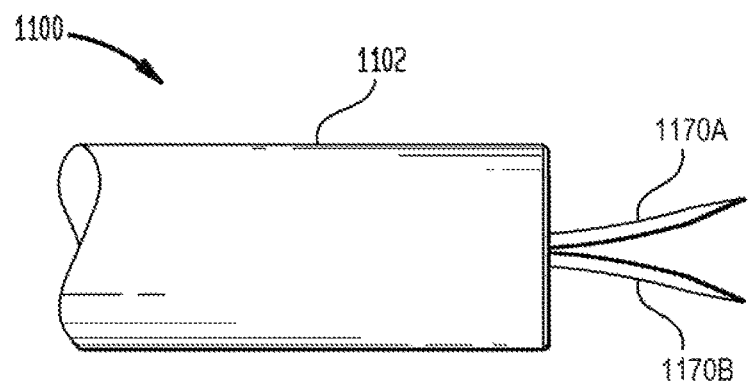
FIG. 11C is a side view of a biopsy device having anchoring elements in accordance with one embodiment of the present disclosure.
Figure 11D:
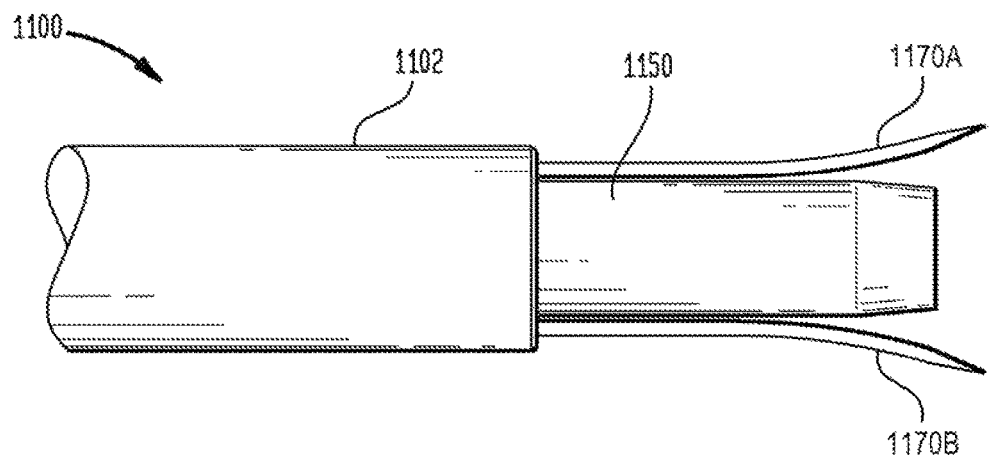
FIG. 11D is a side view of the embodiment of a biopsy device shown in FIG. 11C.

FIGS. 11C and 11D are front perspective views of a distal region of embodiments of an endoscopic biopsy device 1100 having extendible anchoring elements 1170A, 1170B. Anchoring elements 1170A, 1170B are configured to both anchor and part away a portion of the target tissue. Anchoring elements 1170A, 1170B are advanced into the tissue to a desired depth. When the anchoring elements reach the target tissue, coring component 1150 is advanced through the navigation catheter 1102 between anchoring elements 1170A, 1170B. The force of the coring component 1150 against the anchoring elements 1170A, 1170B cause the anchoring elements 1170A, 1170B to spread the tissue allowing the coring component 1150 to reach the target tissue. This configuration of anchoring elements 1170A, 1170B and coring component 1150 allows for the sampling of target tissue that may not be located on, or close to, the exterior surface of tissue. In other words, this configuration allows for the sampling of target tissue located at a deeper depth by coring component 1150. Although depicted as a needle, other embodiments of anchoring elements 1170A, 1170B are contemplated. For example, anchoring elements 1170A, 1170B may comprise of a blunt needle or a flat sheet and may completely surround coring component 1150. In embodiments, anchoring elements 1170A, 1170B may have an adjustable radius of curvature.

In yet another embodiment, the navigation catheter 1102 performs a similar function as anchoring elements 1170A, 1170B by spreading the tissue to allow for the coring component 1150 to reach the target tissue. In this configuration, the navigation catheter 1102 is configured to have a tapered end which expands when coring component 1150 is advanced through the navigation catheter 1102.

Figure 12A:
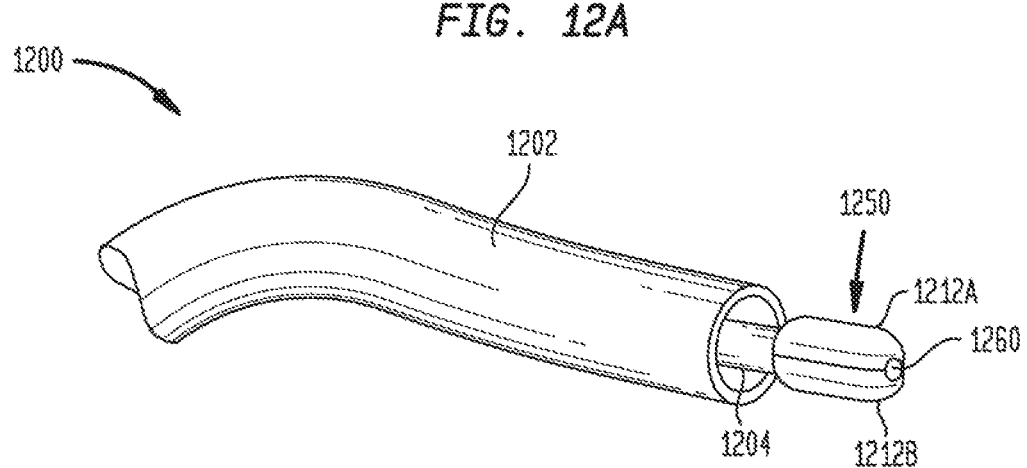
FIG. 12A is a perspective view of a biopsy device having an anchoring element in accordance with one embodiment of the present disclosure.
Figure 12B:
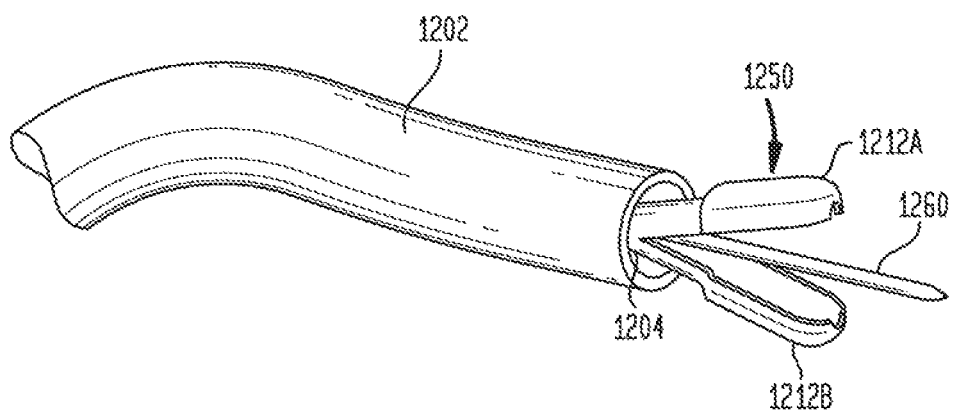
FIG. 12B is a perspective view of the embodiment of a biopsy device shown in FIG. 12A.

FIGS. 12A and 12B illustrate the distal region of an endoscopic biopsy device 1200 in accordance with embodiments of the present disclosure. As shown, biopsy device 1200 is similar to the embodiments described above with reference to FIG. 5 and includes a catheter 1202, and a jaws arrangement 1250. Jaws arrangement 1250 includes a shaft 504 and opposing jaws 512.

FIG. 12A illustrates the configuration of biopsy device 1200 prior to extension of anchoring element 1260 to the target tissue. FIG. 12B illustrates the configuration of biopsy device 1200 and biopsy catheter 1204 following extension of anchoring element 1260, but prior to extension of jaws arrangement 1250 to the target tissue.

As shown, anchoring element 1260 comprises a needle like component, referred to as needle 1260. In these embodiments, a surgeon may extend needle 1260 from within jaws arrangement 1250 such that needle 1260 penetrates a portion of the target tissue and remains secured therein. The needle 1260 can be a shaped like a hook and configured to hook a portion of the tissue sample and pull it closer to the jaw arrangement 1250. In embodiments of the present disclosure, jaws arrangement 1250 samples the portion of the target tissue around needle 1260. More specifically, in the embodiments of FIGS. 12A and 12B, jaws 512 are positioned around the portion of the target tissue attached to needle 1260. As explained above, closure of jaws 512 substantially sever at least the portion of the target tissue attached to needle 1260 from the remainder of the target tissue.

In accordance with certain embodiments shown in FIGS. 12A and 12B, needle 1260 may be extended from jaws arrangement 1250 through an aperture 1262 in jaws 1212. In these embodiments, needle 1260 may be extended to the target tissue without opening jaws 1212. Furthermore, in such embodiments, needle 1260 may be inserted into the target tissue beyond jaws 1212 without interfering with the closure of jaws 1212.

As shown, although anchoring elements illustrated in FIGS. 10-12B have been described herein with reference to certain embodiments and coring components, it should be appreciated that other embodiments are also envisioned. For example, the anchoring elements described may also be used in conjunction with alternative sampling components. As shown, FIGS. 11-12B illustrate the use of a single needle. However, it should also be appreciated that multiple extendible needles may be used in substantially the same manner as described above. It should also be appreciated that in embodiments of the present disclosure, needle 1160, 1260 may bent or straight, solid or hollow wire, and may be integrated or separate from any of catheter 1102, 1202, coring component 1150, 1250 or any other utilized device. In embodiments, the needle 1160, 1260 is a 22 gauge needle.

As shown in FIGS. 11-12B, anchoring element 1160, 1260 extends from within coring component 1150, 1250. However, it should be appreciated that in other embodiments, anchoring element 1160, 1260 may extend from other locations as well, such as adjacent to coring component 1150, 1250. Further, anchoring element 1160, 1260 may rotate and may aid in parting off a tissue sample. Anchoring element 1160, 1260 may also function as a hook to pull back tissue sample.

In alternative embodiments, catheter 1202 is placed directly adjacent target tissue. Anchoring element 1160, 1260 is used to hook onto the target tissue and retracted to pull a portion of the target tissue into the catheter 1202. Coring component 1250 is then used to sever or part-off a tissue sample from the target tissue. In this embodiment, the coring of tissue is performed inside of catheter 1202.

FIG. 13A illustrates a distal region of an endoscopic biopsy device 1300A in which suction 1360A is provided via a biopsy port of the device to secure the biopsy device to the target tissue and or to secure a tissue sample within a coring component. In the embodiments illustrated in FIG. 13A, biopsy device 1300A comprises a catheter 1302 and a coring component 1350A. Extending through a lumen of navigation catheter 1302 is a biopsy catheter 1304 having coring component 1350A disposed at the distal end thereof. Coring component 1350A comprises an element having a longitudinal lumen terminating in a distal opening 1306. In the embodiments of FIG. 13A, a lumen of biopsy catheter 1304 is operationally contiguous with the lumen of coring component 1350A. As described above with reference to FIG. 6, opening 1306 is configured to receive a portion of the target tissue therein, referred to herein as a tissue sample.

FIG. 13B illustrates another embodiment of the present disclosure in which suction is provided via one or more openings in a coring component 1350B of a endoscopic biopsy device 1300B to secure the biopsy device to the target tissue. In the embodiments illustrated in FIG. 13B, biopsy device 1300B comprises a catheter 1302 and a coring component 1350B. Extending through a lumen of catheter 1302 is a biopsy catheter 1304 having coring component 1350B positioned at the distal end thereof. In the embodiments of FIG. 13B, biopsy catheter 1304 and coring component 1350B have a lumen extending longitudinally there through. The lumen terminates in an opening 1306.

In the embodiments illustrated in FIG. 13B, coring component 1350B comprises a plurality of openings 1310 therein. Openings 1310 are substantially perpendicular to a longitudinal axis through the geometric center of opening 1306. Openings 1310 may be microscopic or nanoscopic holes, and may be uniformly disposed on coring component 1350B or randomly disposed. As shown by arrows 1360B, suction is provided via openings 1310. In these embodiments, as coring component 1350B is extended to the target tissue, the suction through openings 1310 causes coring component 1350B to be secured to the target tissue.

FIG. 13C illustrates still other embodiments of the present disclosure in which suction is provided via an endoscopic biopsy device 1300C to secure the biopsy device to the target tissue. In the embodiments illustrated in FIG. 13C, biopsy device 1300C comprises a navigation catheter 1302 and a coring component 1350C. Extending through a lumen 1312 of navigation catheter 1302 is a biopsy catheter 1304 having coring component 1350C positioned at the distal end thereof. In the embodiments of FIG. 13C, biopsy catheter 1304 and coring component 1350C have a lumen extending longitudinally there through. The lumen terminates in an opening 1306.

As shown by arrows 1360C, in the illustrated embodiment, suction is provided around coring component 1350C via lumen 1312. In these embodiments, as coring component 1350C is extended to the target tissue, the suction through lumen 1312 around coring component 1350C causes biopsy device 1300C to be secured to the target tissue. In alternative embodiments, navigation catheter 1302 is placed directly adjacent target tissue forming a near seal with the target tissue. Suction is then used to pull a portion of the target tissue into the navigation catheter 1302. Coring component 1350C is then used to sever or part-off a tissue sample from the target tissue. In this embodiment, the coring of tissue may be performed inside of catheter 1302.

In certain embodiments of the endoscopic biopsy devices described above with reference to FIGS. 13A-13C, the suction through distal opening 1306, openings 1310, and lumen 1312 may be controlled by the surgeon. For example, in certain embodiments the surgeon may control the magnitude of the suction. In other embodiments, the surgeon may disable the suction during or following penetration of coring component 1350A-C. In other embodiments of the present disclosure, the suction continues during penetration of the component. In other embodiments of the present disclosure, the suction continues during penetration of the component. In these embodiments, the suction functions as a retention feature to assist in the removal of the tissue sample from the target tissue.

Although FIGS. 13A-13C have been discussed in reference to coring components 1350, it should be appreciated that in alternative embodiments other sampling components may also be used. For example, in particular embodiments, a jaws arrangement, such as the jaws arrangement described above with reference to FIG. 5 may be used, or coring components as described above with reference to FIGS. 6, 7A-7G, 8A, and 8B.

In one such embodiment in which a jaws arrangement may be used in conjunction with suction, an internal lumen may be included within the jaws arrangement to provide suction at the target tissue between the opposing jaws of the jaws arrangement. In another embodiment, suction may be provided around the jaws via a lumen of a navigation catheter.

Figure 14:
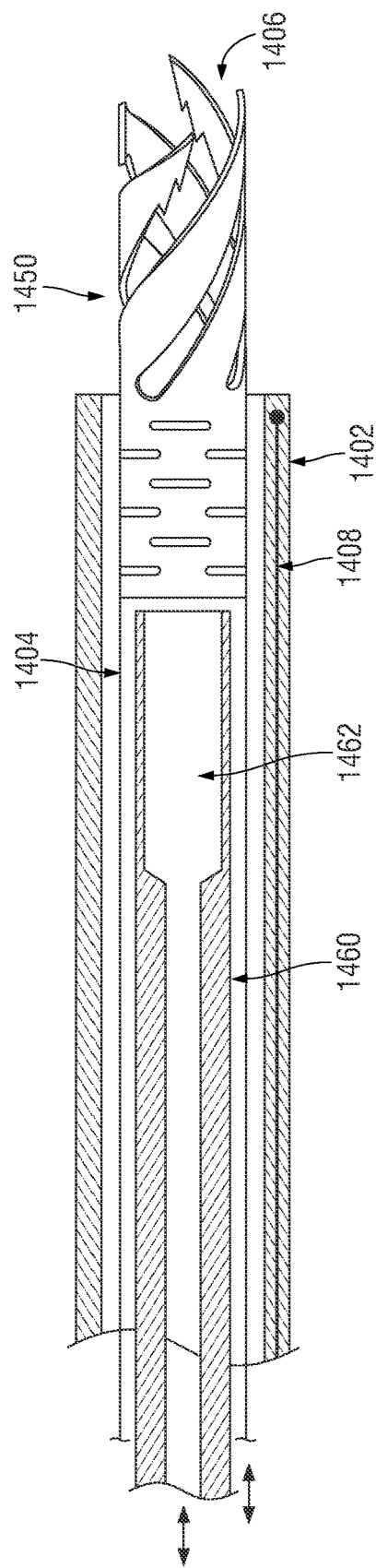
FIG. 14 is a cross section view of a biopsy device having a suction element in accordance with one embodiment of the present disclosure.

FIG. 14 illustrates a cross sectional view of an endoscopic biopsy device 1400 in which suction is provided via a biopsy port of the device to secure the biopsy device to the target tissue and/or to secure a tissue sample within a coring component in accordance with embodiments of this disclosure described above. Endoscopic biopsy device 1400 combines a number of embodiments described above in reference to various FIGS. including FIGS. 4A, 4B, 6, 7A-7G, 8A, 8B, 9A-9F, and 13A-13C. In the embodiments illustrated in FIG. 14, biopsy device 1400 comprises a catheter 1402 and a coring component 1450. Catheter 1402 comprises at least one pull wire 1408 configured to deflect navigation catheter 1402 in a given direction. Extending through a lumen of catheter 1402 is a biopsy catheter 1404 having coring component 1450 disposed at the distal end thereof. Coring component 1450 comprises an element having a longitudinal lumen terminating in a distal opening 1406. In the embodiments of FIG. 14, a lumen of biopsy catheter 1404 is operationally contiguous with the lumen of coring component 1450. As described above with reference to FIG. 6, opening 1406 is configured to receive a portion of the target tissue therein, referred to herein as a tissue sample. Extending through the lumen of biopsy catheter 1404 is a suction tube 1460 having a suction bay 1462 disposed at the distal end thereof for receiving the biopsy sample.

Extendable through the lumen of navigation catheter 1402 is the biopsy catheter 1404 having a coring component 1450 disposed at the distal end thereof. Embodiments of coring component 1450 include those described above with reference to FIGS. 5-8C. Coring component 1450 is also flexible in accordance with embodiments described above with reference to FIGS. 9A-9F.

The endoscopic biopsy device 1400 further provides for suction in accordance with embodiments described above with reference to FIGS. 13A-13C. In the embodiment described in FIG. 14, a suction tube 1460 is extended through the lumen of biopsy catheter 1404. The distal end of suction tube 1460 may further include a suction bay 1462. In these embodiments, as coring component 1450 is extended to the target tissue, the suction through suction tube 1460 and suction bay 1462 causes the coring component 1450 to be secured to the target tissue. Once the target tissue is parted-off from the tissue, the target tissue is aspirated into the suction bay 1462. The suction bay 1462 can then be removed from the lumen of biopsy catheter 1404 for removal by the surgeon. If a further sample is required, a suction tube 1460 can be extended again through the lumen of biopsy catheter 1404 for further parting-off and aspiration of a tissue sample. The suction tube 1460 and suction bay 1462 can also be used to aid in anchoring the endoscopic biopsy device 1400 to the target tissue. In another embodiment, the suction tube 1460 is not necessary and the lumen of biopsy catheter 1404 can act in the same manner as suction tube 1460. That is, a parted-off tissue sample can be aspirated through the biopsy catheter 1404 directly and removed.

Figure 15:
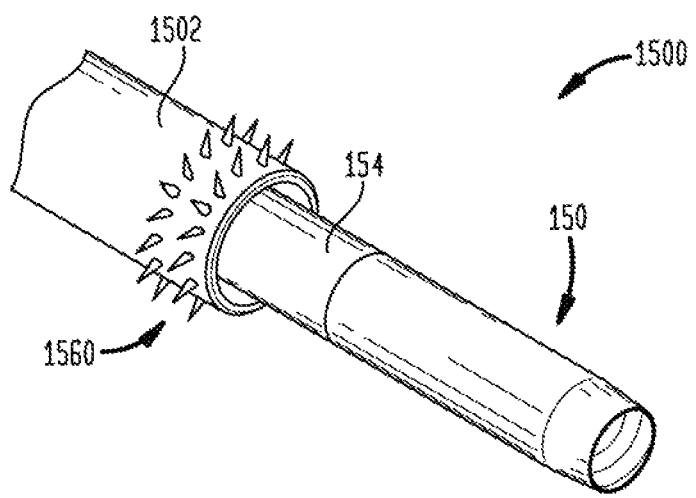
FIG. 15 is a perspective view of a biopsy device having an anchoring element in accordance with embodiments of the present disclosure.

As noted above with reference to FIGS. 3A and 3B, an endoscopic biopsy device in accordance with embodiments of the present disclosure may be anchored or secured to a target tissue prior to sampling of the target tissue. FIG. 15 illustrates a distal portion of embodiments of an endoscopic biopsy device 1500 including an anchoring element 1560, a biopsy catheter 154, and a coring component 150.

In the embodiment of FIG. 15, during insertion of biopsy device 1500 into the patient, coring component 150 is positioned within catheter 1502. Biopsy device 1500 is inserted into the patient until a distal end of catheter 1502 is positioned in contact with a target tissue. While in contact with the target tissue, anchoring element 1560 secures biopsy device 1500 with respect to the target tissue. As shown in FIG. 15, anchoring element 1560 comprises a plurality of spikes 1560 positioned on the distal end of catheter 1502. When catheter 1502 is placed in contact with the target tissue, spikes 1560 attach or secure catheter 1502 to the target tissue. Spikes 1560 are configured to remain attached to the target tissue at least until coring component 150 penetrates the target tissue. Spikes 1560 are further configured to be detached from the target tissue with minimal damage to the target tissue. In certain embodiments, spikes 1560 may be retractable.

In certain embodiments, spikes 1560 are fixed spikes positioned permanently at the distal end of catheter 1502. In other embodiments, spikes 1560 comprise retractable spikes configured to be extended from, and withdrawn into, catheter 1502. In other embodiments, spikes 1560 may be nanoscopic, microscopic, macroscopic, etc.

Although FIG. 15 has been discussed herein with reference to spikes 1560, it should be appreciated that anchoring element 1560 may further comprise a variety of additional embodiments. For example, in certain embodiments, anchoring element 1560 may comprise a textured surface positioned at the distal end of catheter 1502. In these embodiments, the surface of the distal end of navigation catheter 1502 may be modified so that catheter 1502 will adhere to the target tissue. This may include one or more rough portions, barbs etc.

In other embodiments, anchoring element 1560 may comprise an adhesive applied to the distal end of catheter 1502. For example, in such embodiments a reusable adhesive, such as a Gecko-Mussel adhesive may be used. Furthermore, although FIG. 15 has been discussed with reference to an anchoring element 1560 positioned at the distal end of catheter 1502, it should also be appreciated that coring component 150 may have an anchoring element 1560 positioned thereon. In these embodiments, catheter 1502 may be positioned adjacent the target tissue and coring component 150 would be at extended to the target tissue. Prior to penetration of the target tissue by coring component 150, anchoring element 1560 on catheter 1502 would engage the target tissue. In such embodiments, anchoring element 1560 retains coring component 150 in position with respect to the target tissue during initial penetration. Anchoring element 1560 of such embodiments may include any of the anchoring elements discussed above, including rough surface portions, spikes, barbs, adhesive, etc. In certain such embodiments, the one or more blades of coring component 150 may act alone to anchor coring component 150 to the target tissue prior to penetration.

Figure 16A:
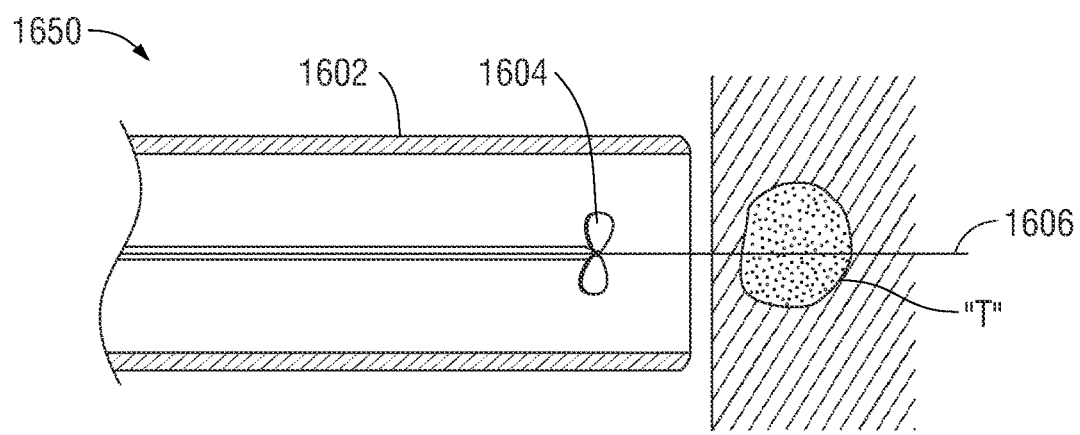
FIG. 16A is a side view of a coring component in accordance with one embodiment of the present disclosure.
Figure 16B:
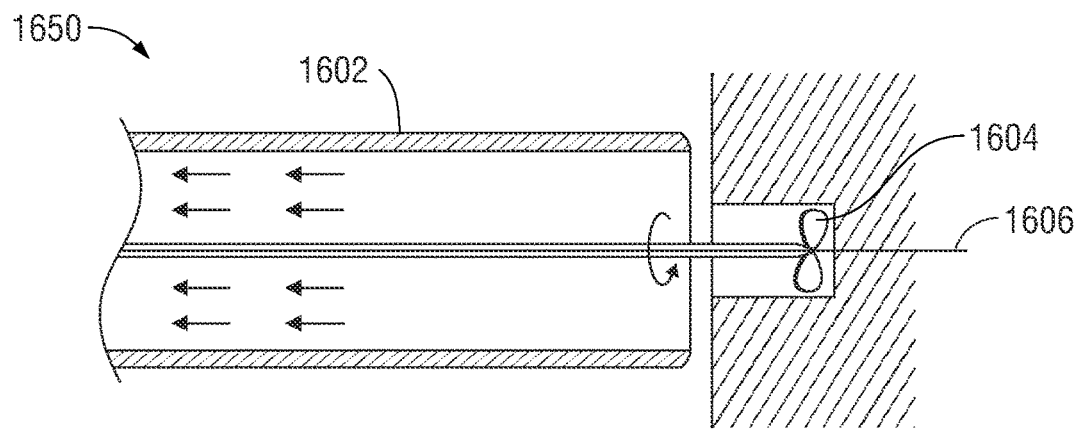
FIG. 16B is a side view of a coring component in accordance with one embodiment of the present disclosure.

FIGS. 16A and 16B illustrate another embodiment of a coring component 1650 used in conjunction with a suction device. Coring component 1650 comprises a navigation catheter 1602, a morcellator 1604, and an anchor 1606. Coring component 1650 is placed adjacent target tissue "T." In one embodiment, anchor 1606 is advanced to anchor the coring component to the target tissue "T." The morcellator 1604 is turned on and advanced into the target tissue "T". As depicted in FIG. 16, the morcellator 1604 is a rotational blade, however, other embodiments of the morcellator are also imagined. For example, morcellator 1604 may comprise a screw, auger, turbine, grinder, file, rotational cutter, etc. As the morcellator 1604 is activated and advanced into the target tissue "T," suction is also activated. The morcellator 1604 parts off pieces of the target tissue "T" which is then aspirated back for sampling through the navigation catheter 1602 by the suction device (as depicted by the arrows in FIG. 16B). In embodiments, the morcellator 1604 advances a predetermined depth. For example, the morcellator 1604 may advance a depth ranging from 1 mm to 10 cm. The morcellator 1604 is then retracted back through the navigation catheter 1602.

Figure 17A:
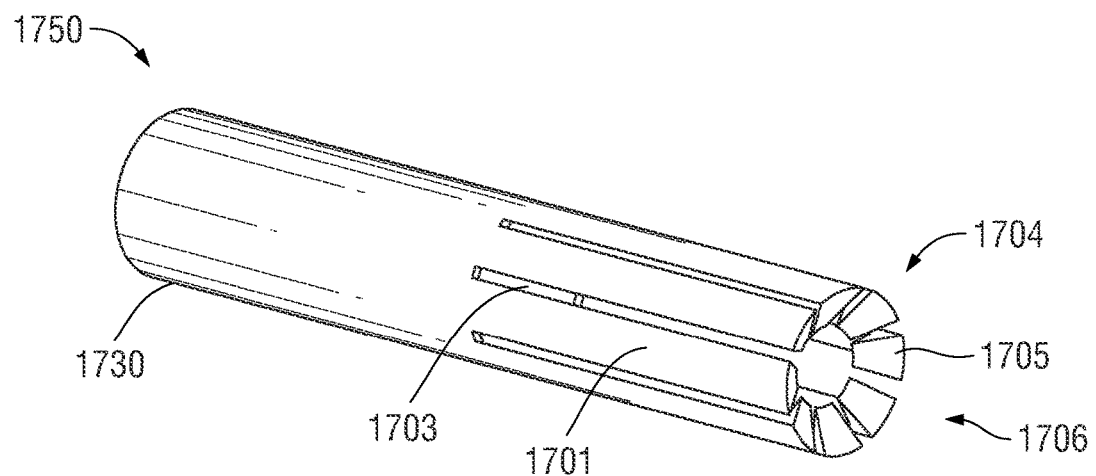
FIG. 17A is a perspective view of a biopsy device having a plurality of expandable blades in accordance with embodiments of the present disclosure.
Figure 17B:
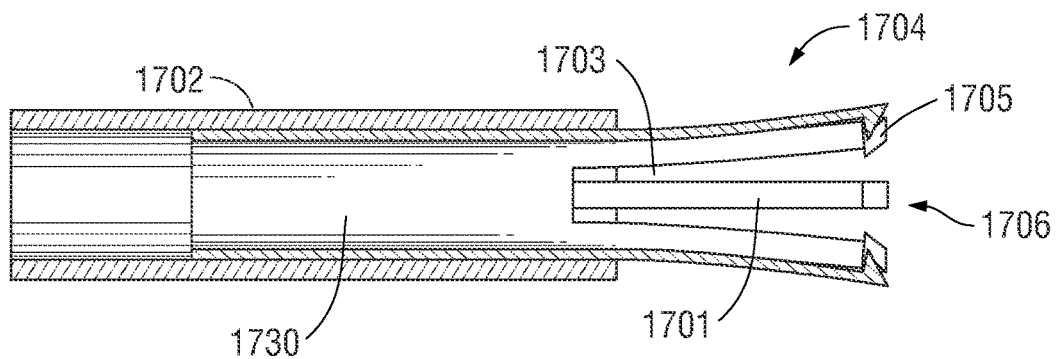
FIG. 17B illustrates a side view of a biopsy device as it is advanced through a distal end of navigation catheter.

FIGS. 17A and 17B illustrate another embodiment of a coring component 1750 in accordance with particular embodiments of FIG. 6. As shown in FIG. 17A, coring component 1750 comprises an elongate element having longitudinal lumen terminating in a distal opening 1706. A distal region of coring component 1750 is formed of a blade arrangement 1704.

As shown in FIG. 17A, blade arrangement 1704 comprises an elongate shaft 1730 and a plurality of distally extending blades 1701 having their distal ends positioned around opening 1706 of coring component 1750. In some embodiments, the distal ends of blades 1701 are radially positioned around opening 1706. The distal end of each blade 1701 is a cutting edge 1705 and contains directional barbs to aid in hooking and parting-off of tissue sample. It should be appreciated that each blade 1701 may also include additional cutting edges. For example, each blade may include one or more longitudinally extending cutting edges 1703. As described further below, when unrestricted, the blades 1701 naturally expand radially (as shown in FIG. 17B).

FIG. 17B illustrates the coring component 1750 as it is advanced through the distal end of navigation catheter 1702. When coring component 1750 is enclosed in navigation catheter 1702, the blades 1701 of coring component 1750 are restricted (as shown in FIG. 17A). However, when the coring component 1750 advances past the distal end of navigation catheter 1702 during coring and sampling, the blades 1701 are unrestricted and naturally expand radially (as shown in FIG. 17B).

In the same or other embodiments, coring component 1750 is advanced through navigation catheter 1702 to the target tissue. The coring component 1750 is then advanced past the distal end of navigation catheter 1702 to substantially sever the target tissue. Upon advancing past the distal end of navigation catheter 1702, unrestricted blades 1705 naturally expand radially. To aid in parting-off and severing of the tissue sample, the navigation catheter 1702 is then advanced over the blades 1705 to constrict blades 1705. The coring component 1750 may then be manually rotated to help in parting-off tissue sample. Additionally, the barbed ends of blades 1705 help to anchor and part-off tissue sample when blades 1705 are restricted radially inwards by the advancement of navigation catheter 1702.

The configurations described above with reference to FIG. 6 and FIGS. 7A-7D can also be equally applied to coring components described in FIGS. 17A and 17B. In particular, the methods of tissue retention, severing, and extraction described above with reference to coring component 760 may also be applicable to coring component 1750.

An endoscopic biopsy device in accordance with embodiments of the present disclosure may be further configured to deliver a treatment to the target tissue prior to, during, or after sampling of the target tissue. The treatment delivered to the target tissue may take a variety of forms. In certain embodiments of the present disclosure, the biopsy device may be configured for hemostasis. For example, in one such embodiment, the biopsy device may be configured to cauterize the tissue at or near the sample during or after the sampling with the sampling component. In alternative embodiments, the biopsy device may be configured to apply a hemostasis coating at or near the sample site to reduce the loss of blood. This coating may be applied in a variety of ways including by applying an agent to the biopsy sampling component prior to the sampling process, or by spraying, injecting, misting or swabbing an agent onto the tissue. As such, a variety of coating mechanisms may be incorporated into the biopsy device. Alternatively, the hemostasis agent may be incorporated into an anchoring mechanism, including the various embodiments described above.

In other embodiments of the present disclosure, biopsy device may be further configured to deliver a therapeutic agent, marker or other material to the target tissue. As described above with reference to FIGS. 5 and 6, the catheter and sampling component may have a lumen extending there through. As such, the therapeutic agent, marker, diagnostic agent, hemostasis agent or other material may be delivered via the lumen extending through catheter and sampling component. These treatments may include, for example, antiseptic, anesthesia, antibacterial or cleaning agents, rinse solutions, genetic or other material in a solid, liquid, solution, gel, vapor, gas or any other form.

In still other embodiments, the biopsy device may be further configured to be to suture the sample site following sampling. This suturing may be done by the coring component, or by one or more components extending from in or near the coring component. As noted above with reference to FIGS. 5 and 6, the catheter and sampling component may have a lumen extending there through. As such, an additional component for suturing the target tissue may be inserted through this lumen.

As noted above, such treatments may be delivered through the contiguous lumens of the catheter and the sampling components. In other embodiments, an additional lumen may be provided through the catheter and sampling component so as to provide an alternate channel for delivery of treatments or which may otherwise be utilized by a surgeon.

Furthermore, while various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments, but should be defined only in accordance with the following claims and their equivalents. All patents and publications discussed herein are incorporated in their entirety by reference thereto.

What is claimed is:

1. A biopsy assembly comprising:
    a biopsy catheter having a proximal portion and a distal portion;
    a navigation catheter configured to receive the biopsy catheter for positioning the biopsy catheter adjacent target tissue;
    a coring component including:
        a distal portion formed of two or more distally extending spiral blades disposed radially around a longitudinal center of the coring component;
        a spiral slit defined between two spiral edges of two adjacent blades of the two or more distally extending blades; and
        a proximal portion being coupled to the distal portion of the biopsy catheter,
        wherein the two or more blades are configured to penetrate the target tissue and sever a tissue sample from the target tissue, and wherein the spiral slit is configured to enable movement of the two or more distally extending blades towards the longitudinal center of the coring component to reduce a diameter of the distal portion of the coring component when the coring component is retracted from the target tissue; and an anchor to anchor the biopsy catheter to the target tissue.

2. The biopsy assembly according to claim 1, wherein the navigation catheter is configured to be received within a working channel of an endoscope.

3. The biopsy assembly according to claim 1, wherein the biopsy catheter and the coring component have a continuous lumen therein.

4. The biopsy assembly according to claim 3, further comprising a suction device coupled to the proximal portion of the biopsy catheter and configured to provide suction to the distal portion of the coring component.

5. The biopsy assembly according to claim 4, further comprising a suction tube having a distal portion and a proximal portion, the proximal portion of the suction tube being coupled to the suction device and the distal portion of the suction tube configured to secure the tissue sample.

6. The biopsy assembly according to claim 5, wherein the distal portion of the suction tube includes a suction bay configured to hold the severed tissue sample.

7. The biopsy assembly according to claim 1, wherein the navigation catheter is flexible.

8. The biopsy assembly according to claim 7, wherein the navigation catheter contains one or more pull wires having a distal portion and a proximal portion configured to cause a distal portion of the navigation catheter to deflect in at least one direction.

9. The biopsy assembly according to claim 7, wherein the proximal portion of the biopsy catheter is coupled to a handle configured to rotate the biopsy catheter.

10. The biopsy assembly according to claim 7, further comprising a pull wire, wherein a distal portion of the pull wire is coupled to a distal portion of the navigation catheter and a proximal portion of the pull wire is coupled to a controller configured to cause the distal portion of the navigation catheter to deflect in one or more directions.

11. The biopsy assembly according to claim 1, wherein the proximal portion of the coring component defines at least one slit configured to provide the coring component flexibility to deflect in at least one direction.

12. The biopsy assembly according to claim 1, wherein the proximal portion of the coring component defines a first longitudinally extending row of slits and a second longitudinally extending row of slits offset relative to the first longitudinally extending row of slits configured to provide the coring component flexibility to deflect in at least one direction, wherein each slit of the first longitudinally extending row of slits and the second longitudinally extending row of slits are perpendicular to a longitudinal axis of the coring component.

13. The biopsy assembly according to claim 1, wherein the proximal portion of the coring component defines at least one row of parallel slits with equal length.

14. The biopsy assembly according to claim 1, wherein the anchor comprises a first needle and a second needle.

15. The biopsy assembly according to claim 14, wherein the coring component is configured to advance through the navigation catheter between the first needle and the second needle.

16. The biopsy assembly according to claim 1, wherein the anchor is a needle having a proximal end and a distal end, wherein the distal end of the needle is curved.

17. A biopsy assembly comprising:
a navigation catheter; and
a biopsy catheter configured to be received within the navigation catheter for positioning the biopsy catheter adjacent target tissue and having a coring component, the coring component including:
a distal portion formed of two or more distally extending spiral blades disposed radially around a longitudinal center of the coring component; and
a spiral slit defined between two spiral edges of two adjacent blades of the two or more distally extending blades,
wherein the spiral slit is configured to enable movement of the two or more distally extending blades towards the longitudinal center of the coring component to reduce a diameter of the distal portion of the coring component when the coring component is retracted from the target tissue.

18. The biopsy assembly according to claim 17, further comprising a plurality of slits, separate from the spiral slit, defined along a proximal portion of the coring component.

19. A biopsy assembly comprising:
a navigation catheter; and
a biopsy catheter configured to be received within the navigation catheter for positioning the biopsy catheter adjacent target tissue and having a coring component, the coring component including:
a proximal portion defining a first longitudinally extending row of slits and a second longitudinally extending row of slits offset relative to the first longitudinally extending row of slits configured to provide the coring component flexibility to deflect in at least one direction; and
a distal portion formed of two or more distally extending spiral blades disposed radially around a longitudinal center of the coring component, the distal portion including a slit defined between two edges of two adjacent spiral blades of the two or more distally extending spiral blades to enable movement of the two or more distally extending spiral blades towards the longitudinal center of the coring component to reduce a diameter of the distal portion of the coring component when the coring component is retracted from the target tissue.

20. The biopsy assembly according to claim 19, wherein each slit of the first longitudinally extending row of slits and the second longitudinally extending row of slits is perpendicular to a longitudinal axis of the coring component.

* * * * *